(12) United States Patent
Mangeot et al.

(10) Patent No.: US 8,697,439 B2
(45) Date of Patent: *Apr. 15, 2014

(54) DIRECT PROTEIN DELIVERY WITH ENGINEERED MICROVESICLES

(75) Inventors: Philippe Mangeot, Lyons Cedex (FR); Vincent Lotteau, Lyons Cedex (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/505,506

(22) PCT Filed: Nov. 10, 2010

(86) PCT No.: PCT/EP2010/067200
§ 371 (c)(1),
(2), (4) Date: Sep. 7, 2012

(87) PCT Pub. No.: WO2011/058052
PCT Pub. Date: May 19, 2011

(65) Prior Publication Data
US 2012/0322147 A1 Dec. 20, 2012

(30) Foreign Application Priority Data
Nov. 13, 2009 (EP) .................................. 09306091

(51) Int. Cl.
*C12N 5/07* (2010.01)
*C12N 5/10* (2006.01)

(52) U.S. Cl.
USPC .......................................... 435/348; 435/325

(58) Field of Classification Search
USPC .................................. 435/348, 325
See application file for complete search history.

(56) References Cited

FOREIGN PATENT DOCUMENTS

WO 2006/059141 6/2006

OTHER PUBLICATIONS

Temchura et al. Vaccine 26:3662-3672, 2008.*
Qing et al. J. Virol. 71(7):5663, 1997.*
Abe Akihiro et al., "In vitro cell-free conversion of noninfectious moloney retrovirus particles to an infectious form by the addition of the vesicular stomatitis virus surrogate envelope G protein," J. Virol., 72(8):6356-6361 (1998) XP009131890.
Qing Keyun et al., "Adeno-associated virus type-2 mediated transfer of ecotropic retrovirus receptor cDNA allows ecotropic retroviral transduction of established and primary human cells," J. Virol., 71(7):5663-5667 (1997) XP009143558.
Abe Akihiro et al., "In vitro cell free conversion of noninfectious moloney retrovirus particles to an infectious form by the addition of the vesicular stomatitis virus surrogate envelope G protein," J. Virol., 72(8).6356-6361 (1998) XP009131890.
Burns et al., "Vesicular stornatitis virus G. glycoprotein pseudotyped retroviral vectors: concentration to very high titer and efficient gene transfer into mammalian and nonmammalian cells" Proc. Natl. Acad. Sol. USA, 90:8033-8037 (1993) XP000674.7277.
International Search Report and Written Opinion in PCT/EP2010/067200, dated Feb. 9, 2011.
Liu et al., "Pseudotransduction of hepatocytes by using concentrated pseudotyped vesicular stomatitis virus G glycoprotein (VSV-G)-moloney murine leukemia virus-denved retrovirus vectors: comparison of VSV-G and amphotropic vectors for hepatic gene transfer," J. Virol., 70(4)2497-2502 (1996) XP002957102.
Qing Keyun et al., "Adeno-associated virus type-2 mediated transfer of ecotropic retrovirus receptor cDNA allows ecotropic retroviral transduction of established and primary human cells," J. Viral., 71(7):5663-5667 (1997) XP009143556.
Temchura et al., "Enhancement of immunostimulatory properties of exosomal vaccines by incorporation of fusion-competent G protein of vesicular stomatitis virus," Vaccine, 26(29-30):3662-3672 (2008) XP022735985.

* cited by examiner

*Primary Examiner* — Marcia S Noble
(74) *Attorney, Agent, or Firm* — McAndrews, Held & Malloy Ltd.

(57) ABSTRACT

The present invention relates to direct protein delivery with engineered micro vesicles.

5 Claims, 13 Drawing Sheets

A

Figure 2:
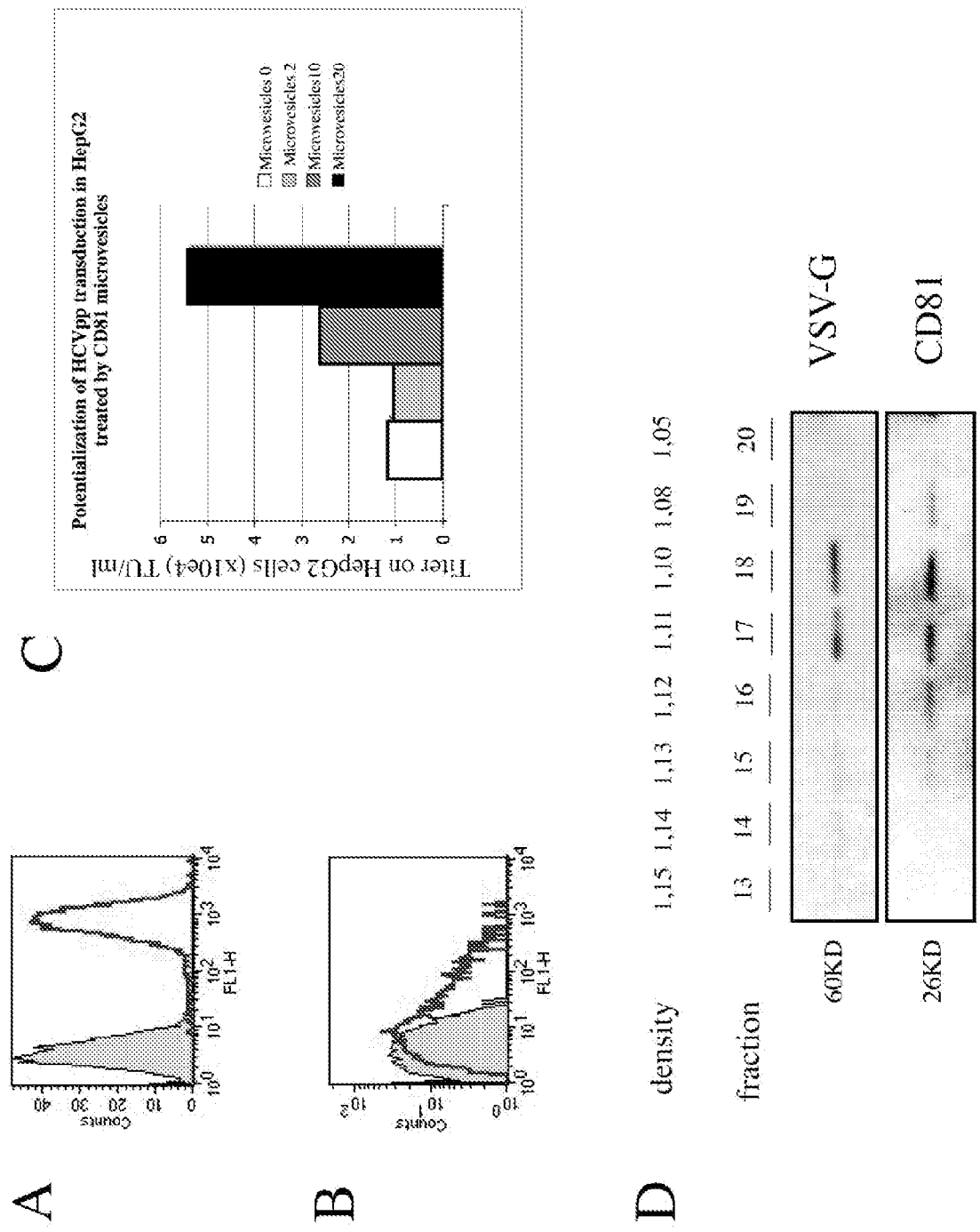

60 KD ▶ VSV G
27 KD ▶ YFP
70 KD ▶ EcoR Flag

Lane  1  2  3  4  5

B

FL1-H

C

Producer Cells | Supernatants

60 KD ▶ VSV G

VSV G protein: wt  w72v cl1  w72v cl2  del  mo    wt  w72v cl1  w72v cl2  del  mo

D

R18 Em590/Cell number

Mock | VSVG | VSVGmut

Figure 1

DIRECT PROTEIN DELIVERY WITH ENGINEERED MICROVESICLES

The present application is filed pursuant to 35 U.S.C. 371 as a U.S. National Phase application of International Patent Application No. PCT/EP2010/067200, which was filed Nov. 10, 2010, claiming the benefit of priority to European Patent Application No. 09306091.1, which was filed on Nov. 13, 2009. The entire text of the aforementioned applications is incorporated herein by reference in its entirety.

FIELD OF THE INVENTION

The present invention relates to direct protein delivery with engineered microvesicles.

BACKGROUND OF THE INVENTION

The transient introduction of proteins of interest into a target cell is a major challenge, with many applications in basic research, applied science and in the therapeutic field.

For decades, introduction of a protein of interest into a target cell has been accomplished indirectly, by the introduction of genetic material encoding said protein of interest, known as transfection.

Many transfection techniques have been developed over the years, such as calcium phosphate transfection, electroporation and lipofection.

However, these techniques have several inconvenients that many limit their use. The introduction of a gene encoding a protein of interest into a target cell relies on the transcription and translation machinery of the target cell. The expression of the desired protein is thus slow, and several undesirable effects can be observed (toxicity of the transfection reagent itself, activation of the interferon response etc.).

Moreover, certain cell types, typically non-dividing cells such as neurons, are poorly transfectable. Other gene transfer techniques known as transduction have been developed more recently in order to circumvent this drawback. Transduction relies on the use of a viral vector to transfer genetic material to a target cell. Retrovirus-based systems are often used to this effect. However, these technologies suffer from several drawbacks. First, there is a sanitary risk associated with the use of retroviral vector, even though said retroviral vectors have been inactivated. Second, production of retroviral particles is very tedious and time-consuming. Indeed, it involves the production of large amounts of 4 or 5 different plasmids which encode the various proteins necessary for the formation of the viral vector particles. Finally, the effects observed in the target cell are not immediate. Typically, the protein of interest is expressed in the target cell after a delay of at least 24 hours, usually 48 to 72 hours, during which the transcription and translation take place.

Previous works described the unexpected transfer of reporter proteins by by-standard agents co-produced with retroviral vectors (Liu et al., Journal of virology 70, 2497-2502 (1996); Gallardo et al., Blood 90, 952-957 (1997). For example, these authors described the ability of their viral preparation to deliver β-Galactosidase in target cells known to be non-permissive to retrovirus mediated gene transfer. This undesirable transduction artefact termed as pseudotransduction led to a transient expression of the transferred protein in the treated cell while retroviral transduction ensures a stable long term expression of the delivered transgene. Interestingly these authors used retroviral vectors pseudotyped with the G protein of the Vesicular Stomatitis Virus (VSV-G) and observed that pseudotransduction occurred specifically with concentrated VSV-G coated retroviral particles. However, these studies provided no conclusive evidence of the mechanism underlying this protein-mediated pseudotransduction and it was thought that the transferred protein was most likely integrated into the viral envelope (Schnell et al., PNAS, 1996, 93, 11359-11365). This pseudotransduction was therefore thought to be limited to membrane proteins. Moreover, it was believed to be non-dissociable from gene-mediated retroviral transduction.

In order to obtain a specific, time-controlled delivery of a protein of interest into a target cell, another available technique is microinjection into the target cell. However, this technique requires the obtaining of the protein of interest prior to microinjection. Peptides can be obtained by chemical synthesis, whereas bigger proteins will require specific production and purification procedures. Thus, these methods are costly and poorly amenable to large-scale uses.

Other studies have focused on the delivery of proteins by conjugating them with a short peptide that mediates protein transduction, such as HIV tat and poly-arginine. However, these techniques are also difficult to implement on a large-scale basis, since they rely on recombinant proteins.

Thus, there is still a need in the art for a fast, safe and efficient method for delivering a protein of interest into a target cell.

SUMMARY OF THE INVENTION

The present invention relates to a eukaryotic cell overexpressing a viral membrane fusion protein and a protein of interest.

The present invention also relates to a microvesicle secreted by a eukaryotic cell according to the invention, wherein said microvesicle comprises said viral membrane fusion protein and said protein of interest.

The present invention also relates to an in vitro method for delivering a protein of interest into a target cell by contacting said target cell with a microvesicle according to the invention comprising said protein of interest.

DETAILED DESCRIPTION OF THE INVENTION

The inventors have discovered that the overexpression of a viral membrane fusion protein in a eukaryotic cell expressing a protein of interest can lead to the secretion of microvesicles comprising said membrane fusion protein and said protein of interest. Further, the inventors have demonstrated that said microvesicles can be used to efficiently deliver said protein of interest to a target cell, without altering the function of said protein. The method of the present invention is thus suitable for the transient and rapid introduction of a functional protein in a target cell.

Thus, the present invention relates to a eukaryotic cell overexpressing a viral membrane fusion protein and a protein of interest. Said eukaryotic cell is capable of secreting microvesicles comprising said viral membrane fusion and said protein of interest.

In one embodiment, the eukaryotic cell according to the invention does not express any viral structural protein and the microvesicles secreted by such eukaryotic cells do not comprise any viral structural protein. Accordingly, the microvesicles according to the invention differ in that aspect from the virus-like particles (VLPs) described in the art, for example, in WO2006/059141, said VLPs comprising viral structural proteins, such as HIV1 Gag.

As used herein, the term "viral structural protein" refers to viral proteins that contribute to the overall structure of the capsid protein or of the protein core of a virus. The term "viral structural protein" further includes functional fragments or derivatives of such viral protein contributing to the structure of a capsid protein or of protein core of a virus. An example of viral structural protein is HIV1 Gag. The viral membrane fusion proteins are not considered as viral structural proteins. Typically, said viral structural proteins are localized inside the microvesicles.

The inventors have indeed shown that microvesicles comprising a protein of interest can be produced in eukaryotic cells that do not express any viral structural protein but overexpress a membrane fusion protein, such as VSV-G or other fusogenic proteins, and said protein of interest.

Moreover, the microvesicles according to the invention may not contain any nucleic acid encoding for the protein of interest. Of course, it can not be excluded that traces of nucleic acids are contained in said microvesicles, in particular traces of mRNA from producer cells or even DNA resulting from previous transfection. However, the inventors have demonstrated that such traces of nucleic acids (if they exist) cannot be responsible for at least 90% of the protein function transfer by microvesicles.

Typically the eukaryotic cell is a mammalian cell, such as a human cell, a chicken cell or an insect cell. Examples of suitable mammalian cells are, but are not limited to HEK-293T cells, COS7 cells, Hela cells and HEK-293 cells. Examples of suitable insect cells include, but are not limited to, High5 cells and Sf9 cells. Insect cells present several advantages. In particular, they are devoid of undesirable human protein, and their culture does not require animal serum.

By "overexpressing", it is meant any means known in the art to enhance the amount of protein expressed by a given cell. Practically, the viral membrane fusion protein and the protein of interest are expressed in said eukaryotic cells to a level so that said eukaryotic cells are capable of secreting microvesicles comprising said viral membrane fusion protein and said protein of interest without the need of expressing any viral structural protein.

Typically, the overexpression of the viral membrane fusion protein and of the protein of interest may be achieved by transfecting the eukaryotic cell with an expression vector encoding the viral membrane fusion protein and an expression vector encoding the protein of interest.

In another embodiment, said eukaryotic cell according to the invention is overexpressing VSV-G as a viral membrane fusion protein and a protein of interest but does not overexpress any other viral proteins, in particular any viral structural protein. The microvesicles secreted according to said embodiment comprise VSV-G and said protein of interest but do not comprise any viral structural protein.

In another specific embodiment, the eukaryotic cells overexpress only the viral membrane fusion protein and said protein of interest. In this embodiment, expression of the viral membrane fusion protein, for example VSV-G, may represent at least 30%, for example at least 50%, of the overexpressed proteins in the cells.

In one embodiment, said viral membrane fusion protein and said protein of interest can be encoded by two different vectors.

In one embodiment, said viral membrane fusion protein and said protein of interest can be carried by a single vector containing a bicistronic expression cassette. In a related embodiment; said viral membrane fusion protein and said protein of interest are not covalently bonded together.

In one embodiment, expression vectors may include episomal replicating plasmids and, for example, plasmids comprising origin sequence of viral nature such as SV40 ORI or EBV ORI sequences.

Overexpression via expression vectors can comprise any gene transfer method known in the art of molecular biology. In a preferred embodiment, overexpression is obtained by transfection of an exogenous DNA. Suitable transfection methods are classical methods known to the skilled person, such as calcium phosphate transfection, transfection using liposomes (also known as lipofection) or electroporation. It falls within the ability of the skilled person to select the appropriate transfection method for a given cell.

In a preferred embodiment, overexpression is not obtained by viral transduction.

Overexpression can be transient overexpression or stable overexpression.

When transient overexpression is used, cells typically overexpress optimum amounts of the viral membrane fusion protein and/or the protein of interest between 48 and 72 hours post-transfection.

The term "overexpression" also covers the overexpression of an endogenous protein, i.e. a protein which is naturally expressed by the eukaryotic cell. The overexpression can consist either in the introduction of additional copies of the gene encoding said protein or in the stimulation of the expression of the endogenous protein. By way of example, the eukaryotic cell can be placed under culture conditions known to enhance the expression of said endogenous protein.

In an embodiment of the invention, the eukaryotic cell overexpresses 2 to 5 different proteins of interest.

Typically, said viral membrane fusion protein is a class I viral membrane fusion protein such as the influenza-virus hemagglutinin, a class II viral membrane fusion protein or a class III viral membrane fusion protein (see for review on class III viral membrane fusion protein Backovic et al, Curr Opin Struct Biol 2009, 19(2):189-96 or Courtney et al, Virology Journal 2008, 5:28).

In a preferred embodiment, said viral membrane fusion protein is a class I viral membrane fusion protein.

Examples of class I viral membrane fusion proteins are Baculovirus F proteins, in particular F proteins of the nucleopolyhedrovirus (NPV) genera, such as *Spodoptera exigua* MNPV (SeMNPV) F protein and *Lymantria dispar* MNPV (LdMNPV) F protein.

In a preferred embodiment said viral membrane fusion protein is a class III viral membrane fusion protein.

Examples of class III viral membrane fusion proteins are rhabdovirus G (such as the fusogenic protein G of the Vesicular Stomatatis Virus (VSV-G)), herpesvirus gB (such as the glycoprotein B of Herpes Simplex virus 1 (HSV-1 gB)), EBV gB, thogotovirus G, baculovirus gp64 (such as *Autographa California* multiple NPV (AcMNPV) gp64), and the Borna disease virus (BDV) glycoprotein (BDV G).

In a more preferred embodiment said viral membrane fusion protein is VSV-G or baculovirus gp64. In one embodiment, said viral membrane fusion protein is VSV-G polypeptide as defined in GenBank AN: M35219.1, or any functional fragments or their functional derivatives retaining fusogenic properties.

As used herein, the term "fusogenic" refers to a viral protein that can induce the fusion of the plasma membrane of the microvesicles to the membrane of the target cell.

In an embodiment of the invention, the eukaryotic cell according to the invention further overexpresses a protein which induces membrane budding. In this embodiment, the production of microvesicles is enhanced.

As used herein, the expression "protein which induces membrane budding" refers to any protein which can promote the deformation of lipid bilayers and mediate the formation of vesicles.

The ability of a given test protein to induce membrane budding can be evaluated according to the following in vitro test "A": HEK293T cells are transfected with the test protein or mock-transfected with an empty vector. 20 hours post-transfection the cell media are replaced with R18-containing medium (20 µg/ml). R18, or octadecyl rhodamine B chloride, is a lipophilic compound that binds membranes and emits fluorescence at 590 nm upon excitation at 560 nm. After 6 hours of incubation, to allow R18 incorporation into cell membranes, media are changed from fresh medium without R18. 72 hours post-transfection, media from the transfected cells and from the mock-transfected cells are collected, clarified and analyzed by a fluorometer. The amount of R18-associated fluorescence, normalized to the number of living cells counted by a rezazurin-based assay, reflects the amount of membrane released by the cells in each condition.

A test protein is deemed to induce membrane budding if it increases the amount of R18-associated fluorescence per cell, as measured by the above test "A".

Various cellular and viral proteins are known to induce membrane budding.

Examples of cellular proteins inducing membrane budding are the proteolipid protein PLP1 (Trajkovic et al. 2008 Science, vol 319, p 1244-1247), the clathrin adaptor complex AP1 (Camus et al., 2007. Mol Biol Cell vol 18, p3193-3203), proteins modifying lipid properties such as floppase, scramblase, proteins which facilitate the secretion via a non-classical pathway such as TSAP6 (Yu et al. 2006 Cancer Res vol 66, p4795-4801) and CHMP4C (Yu et al. 2009, FEBS J. vol 276, p2201-2212).

Examples of viral proteins inducing membrane budding are tetherin/CD317 antagonists such as the Vpu protein of HIV (Neil et al. 2008. Nature vol 451, p425-4431) and various viral structural proteins such as retroviral GAG (Camus et al., 2007. Mol Biol Cell vol 18, p3193-3203) and Ebola VP40 (Timmins et al., Virology 2001).

Membrane budding may also be induced by modifying the cell culture conditions of the eukaryotic cell overexpressing a viral membrane fusion protein and a protein of interest, such as temperature, $Ca^{2+}$ concentration, etc.

As used herein, said protein of interest may be any protein or polypeptide that is desired to be transferred to the target cells. In one embodiment, said protein of interest does not comprise any viral membrane fusion protein or any fragment of said viral membrane fusion protein or derivatives retaining fusogenic properties.

Typically said protein of interest may be a heterologous protein, for example a membrane protein, a cytoplasmic protein, a viral protein or a nuclear protein. As used herein, the term "heterologous" means that said protein is not expressed from a gene naturally found in the genome of the eukaryotic cells overexpressing said protein of interest.

Alternatively, said protein of interest may be an endogenous protein, for example, a protein that is naturally expressed in high amounts in certain cell lines. In this embodiment, cell lines naturally expressing a protein of interest in high amounts are genetically engineered to further overexpress the membrane fusion protein, such as VSV-G, so as to produce microvesicles containing said protein of interest and said membrane fusion protein.

Examples of suitable membrane proteins are membrane receptors, CD81, mCAT-1 (Ecotropic receptor), CXCR4 and homing proteins, CD4, CCR5, sialic acid-rich proteins, claudins, CD21, T-cell receptors, B cell receptors, CFTR and TNFR1.

Examples of suitable cytoplasmic proteins are apoptotic factors such as BAX, BID, BAK, BAD, FasL and fluoresecent proteins such as GFP, YPF, Venus, CFP, DsRed, Cherry-Red and DsRed 2.

Examples of viral proteins are tat, rev, gp120, GP41 (HIV-1/2, SIV), vpx (SIV), tax, rex (HTLV-1), EB1, EBNA2, EBNA1, BHRF1 (EBV), NS3, NS5A, NS1, NS2, Core, E1, E2 (HCV), small T, large T antigen (SV40), NS1, Neuraminidase and HA (Influenza).

Examples of nuclear proteins are transcription factors or cofactors, the tTA tetracycline transactivator, VP16 and VP16-containing fusion proteins, the CRE recombinase, Cre-Ert2 recombinase, FLP recombinase or flippase, Hin recombinase, RecA/RAD51, Tre recombinase, meganucleases such as I-Sce1, transcription factors such as GATA-1, FOG, NF-E2, TAL1/SCL, EKLF, FBI-1, RUNX1, PU.1, Retinoic acid Receptor, vitamine-B3 receptor, CCAAT/enhancer-binding proteins, Ikaros, Pax5, Janus Kinase, E2A, Bcl-6, EBF family, Egr 2 and 3, K1F5, TcF4, MyoD, SUM-1, myogenin, myf-5, MRF4, Pitx2, Egr 2 and Egr 3, NFkB, AP1, AP2, POU factors, Sp1/Sp3, bHLH, Engrailed 2, Foxg1, ELF3, Erm, Olf-1, Pax6, alpha-Pal/Nrf-1, Nurr1 and Pitx3.

Advantageously, the inventors have shown that the protein of interest retains its functionality once it has been transferred into the target cell. In particular, said protein of interest is not cleaved in the target cells. For example, said membrane receptor is correctly localised in the cellular membrane after delivery by microvesicles so as to be able to recognize its corresponding ligand. In another embodiment, said protein of interest is a transcription factor or corresponding co-factor that is correctly localised in the nucleus after delivery by microvesicles so as to stimulate or repress the transcription of genes regulated by said transcription factor.

In an embodiment of the invention, the protein of interest may be modified in order to be located at the membrane of the cell.

In one embodiment the protein of interest is fused to the viral membrane fusion protein. Advantageously the protein of interest may be further modified in order to be released from the membrane under acidic condition by introducing a proteolytic cleavage site which is cleavable under acidic conditions Examples of proteolytic cleavage sites which are cleaved under acidic conditions are the fluHA cleavage site, the Nipah virus F protein cleavage site or the cathepsin cleavage site.

In an alternative embodiment, the protein of interest is not fused to the viral membrane fusion protein. Indeed, it has been shown that said protein of interest when overexpressed with the viral membrane fusion protein can be colocalized in the microvesicles. Typically a farnesyl motif responsible for the farnesylation of the protein and/or a myristyl motif responsible for the myristylation of the protein may be introduced in order to direct the protein to the membrane.

In one embodiment, the viral membrane fusion protein and/or the protein of interest can contain a tag which enables the purification of the microvesicles released from the eukaryotic cell. Said tag can be located for example in the ectodomain of the viral membrane fusion protein. Suitable tags include, but are not limited to: Flag tag, HA tag, GST tag, His6 tag. It falls within the ability of the skilled person in the art to select the appropriate tag and the appropriate purification method of said tag. Suitable purification methods include, but are not limited to immunoprecipitation, affinity chromatography, and magnetic beads coated with anti-tag specific antibody.

In a preferred embodiment, a eukaryotic cell according to the invention is virus-free, in particular, said eukaryotic cell does not comprise any nucleic acid encoding a viral structural protein.

The present invention also relates to a microvesicle secreted by a eukaryotic cell according to the invention, wherein said microvesicle comprises said viral membrane fusion protein and said protein of interest. In another embodiment, said microvesicles are obtained from eukaryotic cells according to the invention comprising said protein of interest that is not bonded covalently to said viral membrane fusion protein.

Without wishing to be bound by theory, said microvesicles are considered to be exosome-like and to have a size between 40 and 150 nm, for example between 40 and 100 nm, for example an average size of about 100 nm. Typically a microvesicle according to the invention has a density between 1.08 g/ml and 1.12 g/ml. Preferably a microvesicle according to the invention has a density between 1.09 g/ml and 1.11 g/ml. Typically, said density can be measured by sedimentation on a continuous iodixanol gradient as defined in Example 1.

When transient overexpression of the viral membrane fusion protein and/or of the protein of interest is used, microvesicles are typically harvested from the cell supernatant 48-72 hours post-transfection. Typically, the microvesicles according to the invention may be isolated by filtration (for example on 0.45 µm pore filters) of the cell supernatant of eukaryotic cells according to the invention and ultracentrifugation for example, by ultracentrifugation at 110,000 g for 1.5 hours. Advantageously, the microvesicles according to the invention may be frozen and stored at −80° C. without losing their ability to transfer material to the target cell.

In another embodiment, said microvesicles according to the invention do not comprise any nucleic acid coding for said protein of interest.

In a preferred embodiment, a microvesicle according to the invention is virus free.

Firstly described for immune system cells, microvesicles released from cells are found in vivo in many body fluids (Simpson et al. *Proteomics* 8, 4083-4099 (2008)). Many studies have highlighted the role of these microvesicles in the modulation of the immune response and intercellular communication.

Without wishing to be bound by theory, it is believed that the microvesicles of the invention are exosome-like vesicles, and the presence of the viral membrane fusion protein enables said microvesicles to efficiently deliver the material contained in said microvesicles to the target cell.

The present invention also relates to an in vitro method for delivering a protein of interest into a target cell by contacting said target cell with a microvesicle of the invention comprising said protein of interest.

Examples of target cells are common laboratory cell lines such Hela cells and derivatives, HEK293 cells, HEK293T cells, NIH3T3 cells and derivatives, HepG2 cells, HUH7 cells and derivatives, small lung cancer cells, Caco-2 cells, L929 cells, A549 cells, MDCK cells, THP1 cells, U937 cells, Vero cells and PC12 cells; human hematopoietic cells CD34+ purified from bone marrow, from blood, from umbilical cord; Dendritic Cells (DCs) differentiated from blood monocytes or from CD34+ cells; primary human cells purified from blood including T-cells (CD8 and CD4), B-cells (including memory B-cells), Mast cells, macrophages, DCs, NK-cells; primary murine cells purified from blood including T-cells (CD8 and CD4), B-cells (including memory B-cells), Mast cells, macrophages, DCs, NK-cells; primary human fibroblasts including MRC5 cells, IMR90 cells; primary murine fibroblasts and Embryonic Stem cells (ES) from human, murine, rat, chicken, rabbit origin.

The tropism of the microvesicles of the invention will depend on the tropism of the viral membrane fusion protein used.

For example, VSV-G being a pantropic, microvesicles according to the invention comprising VSV-G will target almost any cells. Microvesicles comprising a viral membrane fusion protein with a tropism for respiratory tract cells will preferably be used to target respiratory tract cells.

In a preferred embodiment the microvesicles according to the invention are produced in situ, by co-culture of the target cells with the microvesicles producing cells. In one specific embodiment, the target cells and the microvesicles producing cells are physically located in two different compartments separated by a porous wall, wherein said porous wall has pores with a diameter smaller than the diameter of eukaryotic cells but bigger than the diameter of the microvesicles of interest. Advantageously, the microvesicles as produced by the eukaryotic cells according to the invention can diffuse from one compartment to the other to reach the target cells where they can deliver the protein of interest.

This technique enables the delivery of protein into target cells, without the need of an isolating step.

Typically several (e.g., 2, 3, 4, 5, 6 . . . ) different proteins of interest may be delivered into a target cell by contacting said target cell with several different microvesicles of the invention comprising said several different proteins of interest.

Typically, the contacting of said several different microvesicles may be simultaneous or sequential.

As opposed to gene delivery achieved by multiple viral vectors, protein delivery with microvesicles according to the invention is an original method to introduce rapidly a function in a targeted cell, without involvement of the transcription machinery or any viral integration processes which limit viral transduction in many cell types. The microvesicles according to the invention could be used in virtually any cell type including resting or fully differentiated cells.

Contrary to classical gene transfer techniques such as gene transfection, the method of the invention does not rely of transcription and translation within the target cell, does not perturb the cell metabolism. Thus, it is believed that the method according to the invention does not activate any interferon response and is therefore a more specific method for delivering a protein of interest to a target cell.

Due to the low amounts of material delivered by the microvesicles according to the invention and to their non-genetic nature, the microvesicles appear to be useful for applications where low and transient presence of proteins may lead to striking biological effects, i.e. to proteins having a high biological penetrance.

The person skilled in the art will readily select the appropriate pairs of protein of interest/target cell, according to each specific goal. Non limitative examples of applications of the cells, microvesicles and method according to the invention are described hereafter.

In one aspect the invention relates to the in vitro use of the microvesicles according to invention.

In one aspect the invention relates to the in vivo use of the microvesicles according to invention.

In one aspect, the invention relates to the use of a microvesicle according to the invention for non-therapeutic applications.

Typically, the microvesicles according to the invention can be used for introducing a protein of interest into a target cell in vitro in order to study the physiological effect of said protein of interest. There are many possible applications of the invention as tool for basic science investigation.

By way of example, the cells, microvesicles, and method according to the invention can be used in order to deliver specific cofactors necessary for the induction of inducible expression systems. Typically proteins of interest include the Cre recombinase (useful for induction of the cre/lox system), the tTA transactivator (useful for induction of the tetracycline operator). Said cofactors are often difficult to introduce into target cells and it is desirable to control precisely the kinetics of the inducible systems by controlling precisely the delivery of the protein of interest.

Another example is the delivery of a cellular protein regulating cell expansion differentiation or death, in an in vitro cellular model. Typically, the cells, microvesicles and methods of the invention can be used to deliver a pro-apoptotic factor such as Bax-2 and to screen for molecules which modulate apoptosis.

The invention also relates to a microvesicle according to the invention for use in therapy.

The invention also relates to a microvesicle according to the invention for use in the prevention of graft rejection.

Certain cell surface proteins have been shown to affect the migratory capacity or the grafting of hematopoietic stem cells (HSC). For instance, transient delivery of CXCR4 can be useful in cell therapy using HSC as homing molecule in order to promote the graft process. It would be undesirable to use a gene transfer, which would result in the transfer of CXCR4 to all descendant cells. On the contrary, the method of the invention enables transient and controlled protein transfer only during the time necessary for the graft to take.

The invention also relates to a method for inducing or potentiating cell differentiation by delivery of transcription factors. In particular, the cells and microvesicles of the invention can be used for megakaryocytic differentiation, myeloid cell differentiation, lymphoid cell differentiation, NK differentiation, astrocyte differentiation, maturation of oligodendrocyte progenitors, muscle cell differentiation, keratinocyte differentiation, retinal differentiation, erythroid cell differentiation, adipocyte differentiation.

Another possible application is the potentiation of viral infection by delivering viral (co)receptors to target cells. For example, the cells and microvesicles of the invention can be used to deliver HCV receptors and coreceptors, HBV receptor, Hemorrhagic fever virus receptors, HIV-1 receptors and coreceptors, and MLV-E receptor.

In particular, the invention relates to the delivery of a receptor, for example a receptor that renders a cell transiently permissive to an ecotropic viral particle.

By way of example, the microvesicles, cells and method of the invention can be used to deliver an ecotropic receptor EcoR (such as m-CAT1) to a target cell in order to render it permissive to an ecotropic virus. Any gene of interest can then be delivered to the target cell (which will express the ecotropic receptor) via an appropriate ecotropic viral construct.

As used herein, the term "ecotropic" has its general meaning in the art. An ecotropic virus is a retrovirus which can replicate only in the host of the species in which it originated. More specifically, the term "ecotropic virus" as used herein refers to a rodent virus that can only replicate in a cell expressing its cognate receptor, the ecotropic receptor EcoR.

Advantageously, said ecotropic virus is safe for the manipulator since it cannot infect human cells other than those which have been targeted by a microvesicle expressing the ecotropic viral receptor.

Typically, said ecotropic virus is a Moloney-based retrovirus and said ecotropic receptor is m-CAT1. An example of a gene coding for m-CAT1 is shown in Genbank accession number NCBI Reference sequence NM_007513.3.

Accordingly, the invention relates to a method for delivering a protein of interest to a cell comprising the steps of:
  delivering an EcoR ecotropic viral receptor to a target cell by a microvesicle comprising a viral membrane fusion protein, for example VSV-G and said EcoR ecotropic viral receptor; and,
  delivering a protein of interest to said target cell by an ecotropic virus comprising at least one gene encoding a protein of interest.

Further, the cells and microvesicles of the invention can be for potentiating viral infection or viral/vector production by delivering trans-actived viral proteins (including HCV proteins, HBV proteins, HIV-1/2 or SIV proteins, Hemorrhagic fever virus proteins, Influenza virus proteins, EBV proteins, SV40 proteins) to virus-producing cells.

Another possible application is the delivery of a receptor that renders a cell transiently permissive to an extracellular signal.

By way of example, the microvesicles, cells and method of the invention can be used to introduce an antiviral TCR into T cells as target cells, and to use said T cells for their antitumoral properties (Cohen et al., Cancer Research, 2007, 67, 3898-3903; Johnson et al. J Immunol. 2006, 177, 6548-6559 and Zhao et al., J Immunol, 2005, 174, 4415-4423).

Thus, the invention also relates to a microvesicle according to the invention for use in the treatment of cancer.

In the field of vaccination, dendritic cells (DC) are often used as antigen-presenting cells in order to stimulate the immune response.

However, dendritic cells do not exist as cell lines and must be obtained by primary culture.

The present invention provides substitute DCs that can be used for vaccination purposes. Indeed, the method of the invention can be used to provide modified producer cell lines that produce microvesicles containing MHC or co-stimulating factors and/or antigens. Said microvesicles can be used for vaccination purposes.

The cells, microvesicles and methods of the invention can also be used to deliver specific antigens to antigen-presenting-cells in order to promote immune response.

In the following, the invention will be illustrated by means of the following examples and figures.

FIGURES LEGENDS

FIG. 1: Incorporation of YFP in VSV-G Carrying Microvesicles (A) Western blot analysis of concentrated microvesicles produced by 293T-YFP transfected by pVSV-G (lane 1), pVSV-G V72 (lane 2), SwFlagEcoR (lane 3), SwFlagEcoR and pVSV-G (lane 4) and mock transfected (lane 5) Immunostainings were performed with Mabs directed against VSV-G (P5D4), the Sigma flag (M2) revealing the tagged version of EcoR and YFP (GSN24).

(B) FACS analysis of cells exposed to the microvesicles from the VSV-G and YFP expressing cells, compared to cells exposed to microvesicles from cells expressing YFP alone.

(C) HEK cells were transfected either by a plasmid encoding the wild-type VSV-G protein (wt) or a fusion-defective mutant W72V (2 DNA clones were tested). A truncated form of VSV-G deleted for its ectodomain was also included in the experiment. 48 h after transfection, supernatants were harvested and cells lysed for a Western blot analysis. All proteins were highly expressed in the producer cells. However, only the wt VSV-G was detected in the supernatant and not the fusion defective mutant.

(D) HEK cells were transfected as above and incubated, 20 hours post-transfection, in a medium containing 0.2 µg/ml of R18, a fluorescent lipophilic compound which binds to membranes, for 6 hours. 72 hours post-transfection, media from the different cell types were collected, clarified and the analyzed by a fluorometer to quantify the amount of R18-associated fluorescence, reflecting the amount of membranes released into the supernatant. Results are given as the R18 value, normalized by the number of living cells.

FIG. 2: Biochemical and Functional Analysis of CD81NSV-G Coated Microvesicles (A) CD81 expression on 293T producer cells. A mouse IgG isotypic control was used (shaded area).

(B) CD81 expression on HepG2 cells exposed to concentrated microvesicles, one hour after treatment. Non-treated HepG2 were labelled as well (grey shaded control).

(C) Potentiation of HCVpp transduction in HepG2 cells treated with various doses of microvesicles. YFO encoding HCVpp were produced in 293 cells and pre-titrated on HUH 7.2 cells at 8×10e4 transduction units (TU) per ml. The figure gives the titers in HepG2 which increases with the amount of microvesicles they have been exposed to.

(D) Density analysis of CD81-bearing microvesicles. Microvesicles were produced in 293T cells cultured with octadecylrhodamine B chloride (R18), a fluorophore labelling membrane lipids. Concentrated microvesicles were laid on a continuous iodixanol gradient and centrifuged 12 hours at 41000 rpm in a SW41 rotor. 20 fractions of 0.5 ml were then collected and ½0 of each fraction was analyzed by Western blot under semi-native conditions. VSV-G and CD81 immunolabellings are shown for fractions 13 to 20 and were absent from other fractions (not shown).

Figure 3:
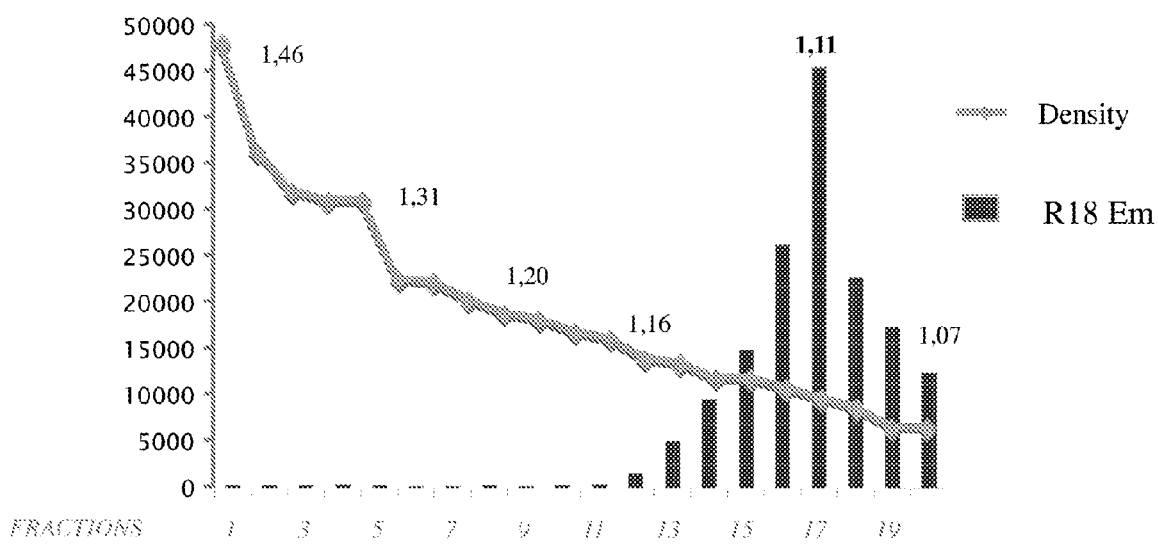
Figure 3:
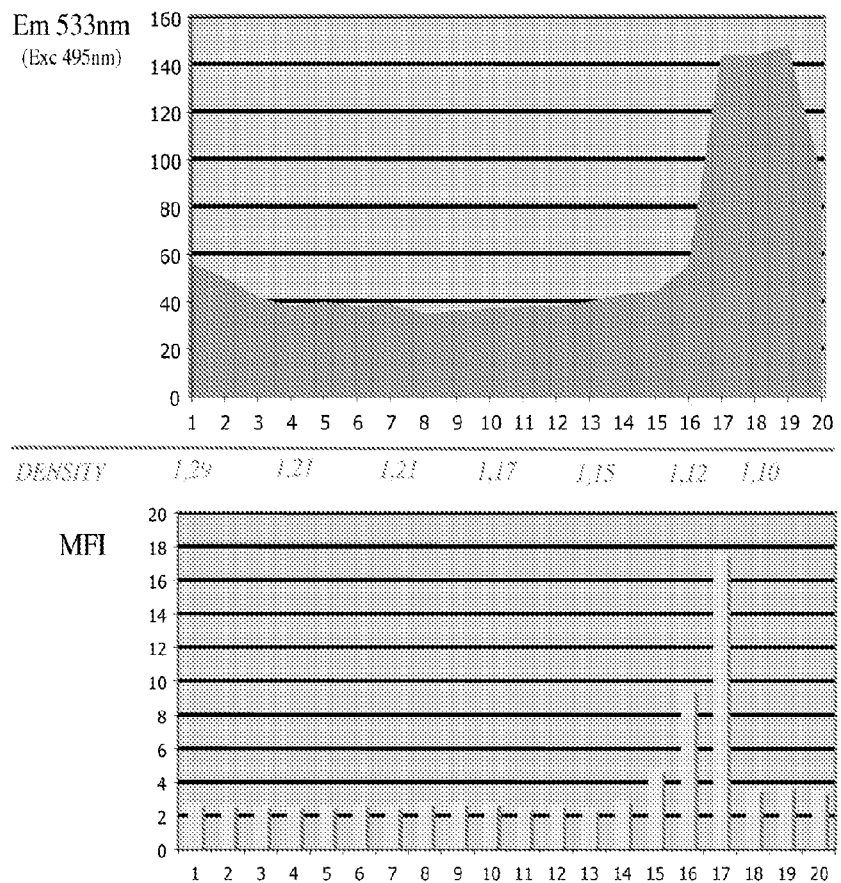

FIG. 3: Characterization of Gesicles (A) Membrane-associated fluorescence in collected fractions upon density iodixanol gradient. Concentrated VSV-G Gesicles were laid on a continuous iodixanol gradient and centrifuged 3 hours. 20 fractions of 500 µl were collected from the bottom of the tube, fraction 1 corresponding to a density of 1.46 and fraction 20 to a density of 1.07 as indicated. ⅕ of each fraction (100 µl) were weighed and transferred to a 96 well plate prior to analysis in a fluorimeter. The figure gives the emission values at 590 nm upon R18 excitation at 560 nm.

(B) Characterization of YFP and CD81 Bearing Gesicles

Top panel: analysis of YFP-associated fluorescence in collected fractions upon density gradient. Concentrated VSV-G Gesicles produced in YFP-positive cells were laid on a continuous iodixanol gradient and centrifuged 3 hours. 20 fractions of 500 µl were collected from the bottom of the tube, fraction 1 corresponding to a density of 1.3 and fraction 20 to a density of 1.09 as indicated. ⅕ of each fraction (100 µl) were weighed and transferred to a 96 well plate prior to analysis in a fluorimeter. The figure gives the emission values at 533 nm upon YFP excitation at 495 nm.

Lower panel: Analysis of YFP pseudotransduction in human cells. ⅒ of each fraction was laid on 1×10e5 HEK cells cultivated in a 12-well plate. 24 hours later, cells were analyzed by FACS. The figure indicates the mean fluorescence intensity (MFI) of each cell population exposed to the different fractions.

Figure 4:
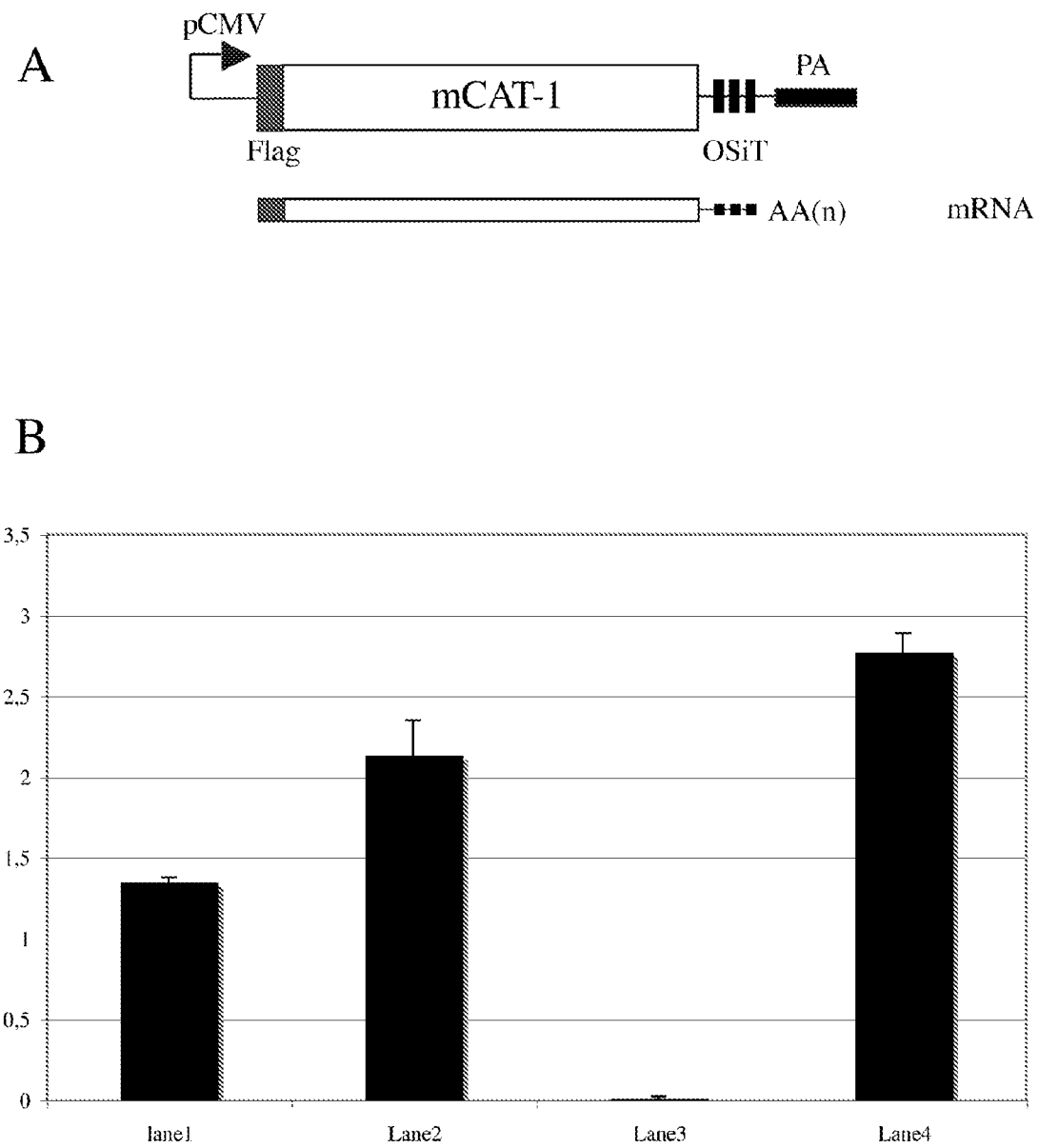

FIG. 4: EcoR Delivery in Human Cells by EcoR-Bearing Gesicles (A) Schematic representation of mCAT-1 encoding plasmid where pCMV stands for the early human cytomegalovirus promoter, USiT for a concatemer of three repeated sequences targeted by a universal siRNA, PA for the SIV polyadenylation signal. The mRNA represented below is equipped with the USiT sequence, which renders it highly sensitive to degradation mediated by universal siRNA.

(B) Titer of GFP-encoding lentiviral vector pseudotyped with the MLV Ecotropic envelope on 293T cells treated with mCAT-1 Gesicles. HEK 293T cell were treated for 1 hour at 37° C. with 2 µg (lane 1) or 4 µg (lane 2) of concentrated Gesicles. After 2 PBS washes, cells were transduced with 100 µl of a preparation of GFP lentivectors pseudotyped with the MLV Ecotropic envelope (lanes 1, 2 and 3) or with the VSV-G envelope (lane 4). Three days after transduction, cells were analyzed by FACS and titers of vector preparation were calculated and are given as means of 3 different transduction assays.

Figure 5:
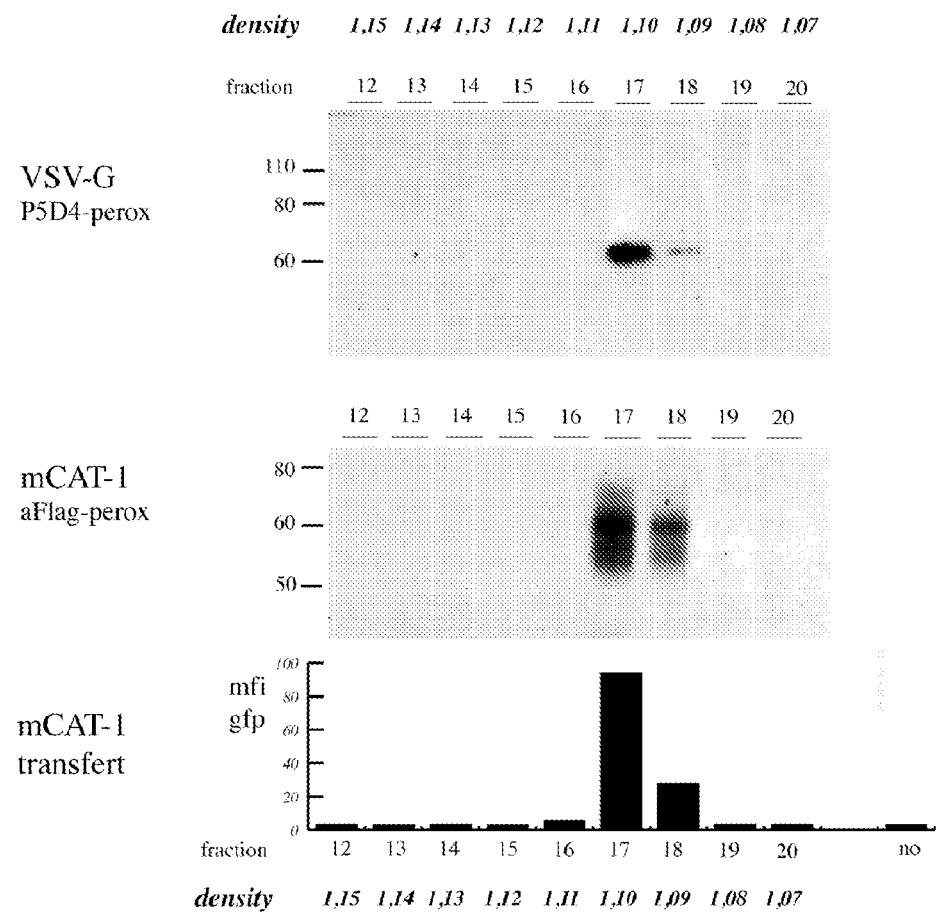

FIG. 5: Biochemical and Functional Analysis of mCAT-1 Bearing Gesicles

Gesicles were prepared upon co-transfection of HEK293T cells by VSV-G and a tagged version of mCAT-1, the receptor for the murine leukaemia virus ecotropic strain. Cell medium was changed 24 h later and collected the day after. Supernatants were clarified prior to an ultracentrifugation at 35000 rpm for 1 h 30 in an SW-41 rotor. The pellet was resuspended in PBS and frozen before the density purification process.

Rate zonal centrifugation through continuous iodixanol gradients: Crude concentrated vesicles were overlaid on a continuous Optiprep gradient (6% iodixanol in 215 mM sucrose, 2 mM EDTA, 10 mM Tris HCL pH8/56.4% iodixanol in 5 mM sucrose, 2 mM EDTA, 10 mM Tris HCL pH8) and centrifuged for 12 hours at 41000 rpm in a SW41 rotor. Fractions (0.5 ml) were collected from the bottom of the gradients and kept at 4° C. before Western blot analysis and the functional assay. Density of the fractions was measured by careful weighing of 100 µl of each fraction.

Protein of fractions 12 to 20 were separated via SDS-PAGE using 4-12% Bis-Tris NuPage gels (Invitrogen) run in MOPS buffer. 5 µl of each fraction were analyzed. After electroblot onto a nitrocellulose membrane, proteins were revealed by a peroxydase-conjugated antibody directed against VSV-G (P5D4 Sigma) diluted at ⅟1000 or a peroxydase-conjugated anti-Flag (Sigma) at ⅟1000, both incubated one hour at room temperature.

To assess the biological activity of fractions, 30 µl of each sample were added to 293T cells seeded at 1×10e5 cells per well in a 24-well plate. One hour later medium was replaced by 200 µl of fresh medium supplemented by 200 µl of supernatant containing GFP-encoding lentivector pseudotyped with the Ecotropic envelope. 48 hours post-transduction cells were trypsinized an fluorescence values (MFI) were analyzed by FACS.

Figure 6:
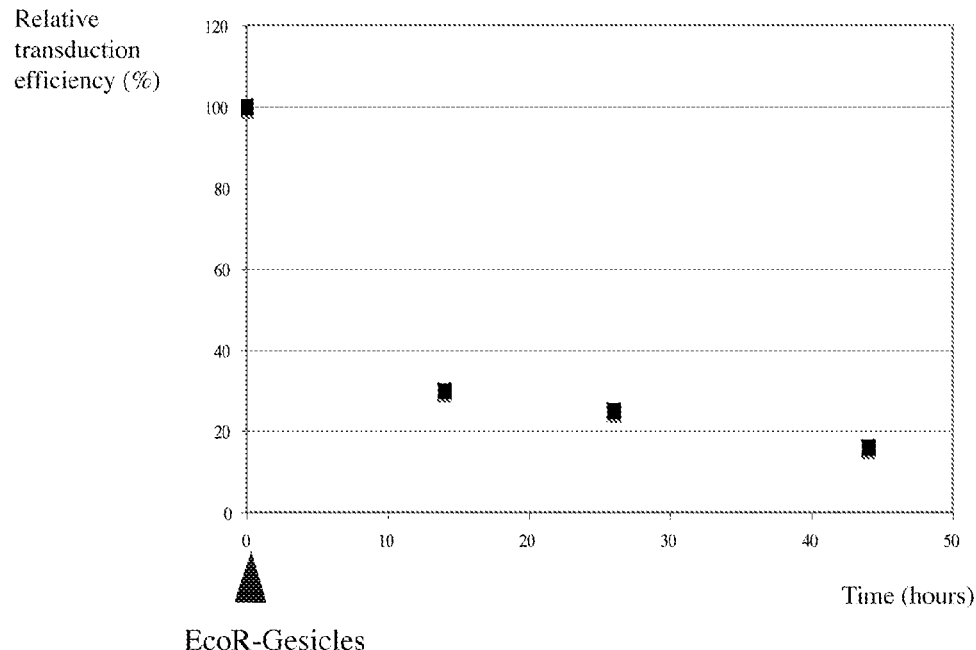

FIG. 6: Disappearance of Transferred mCAT-1 in Gesicle-Treated Human Cells

HEK293T cells were exposed to undersaturant doses of EcoR-Gesicles for 1 hour at 37°. After two washes, cells were transduced with GFP lentivectors pseudotyped with the Ecotropic envelope 5 min, 12 hours, 24 hours or 45 hours after Gesicle exposure. The same transduction assay was performed on 293T cells stably expressing EcoR to measure the progressive decrease of lentivector titer due to target cell division. Results are given as the percentage of transduction efficiency relative to the transduction value obtained at time 5 min (100%). All values were corrected in regard with the cell division rate.

Figure 7:
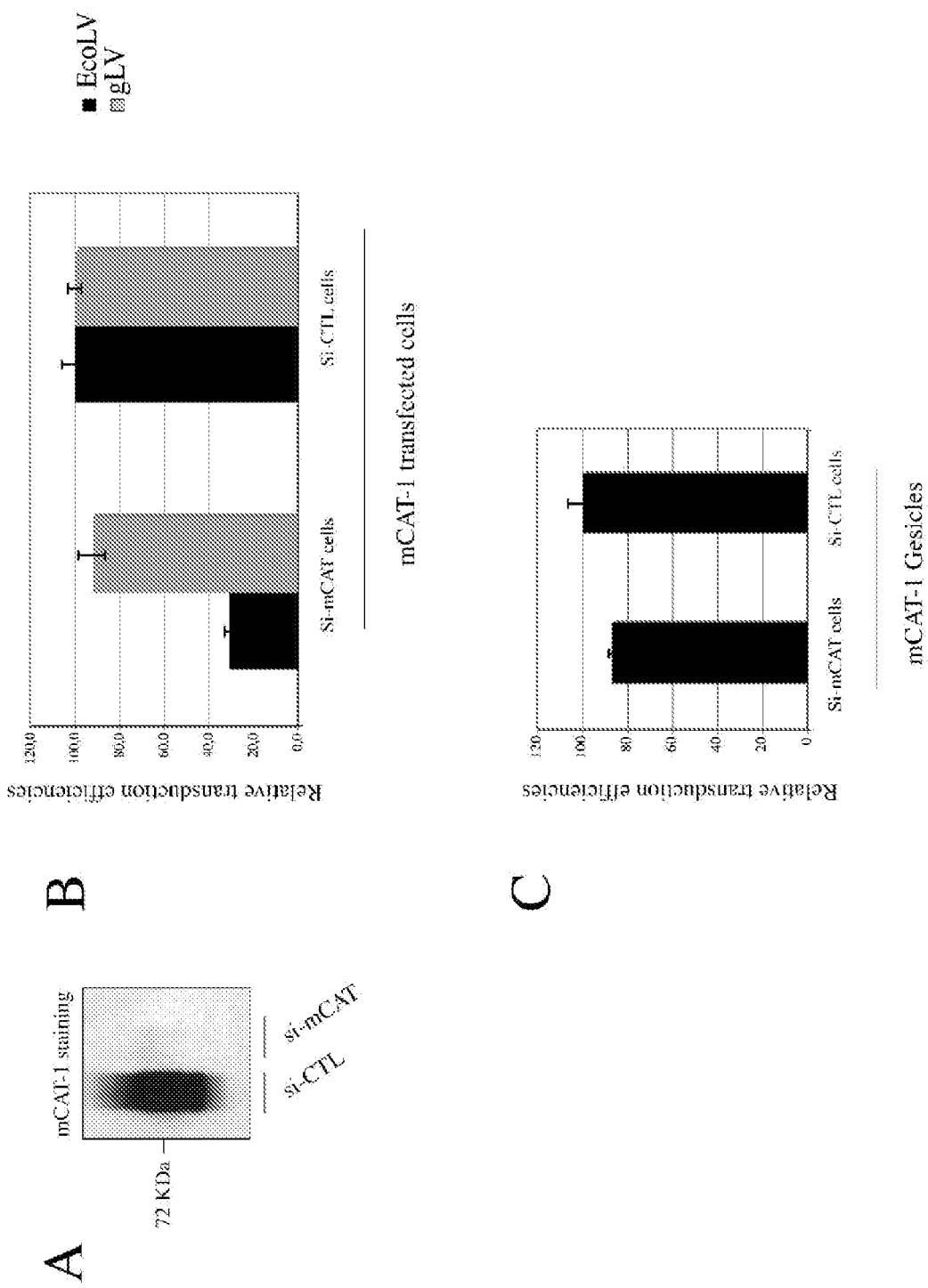

FIG. 7: Specific Degradation of EcoR mRNA does not affect EcoR Function Introduced by Gesicles.

Functional Validation of the si-mCAT.

A synthetic siRNA designed against mCAT-1 was transfected in human cells in addition with a plasmid encoding a flagged mCAT-1. si-mCAT and si-CTL cells were next examined for their expression of mCAT and their permissiveness to transduction with Ecotropic (EcoLV) (black bars) and pantropic control lentiviral vectors (gLV) (grey bars).

(A) mCAT-1 immunostaining in si-CTL and si-mCAT cells (B) Transduction assay with GFP lentivectors in target cells transfected by mCAT-1. Transduction values were analysed by FACS 72 hours post-transduction and were set at 100% efficiency for si-CTL cells. 70% of EcoLV-transduction is inhibited in cells treated with si-mCAT while gLV-mediated transduction is almost unaffected (8% of inhibition).

Specific Degradation of the mCAT mRNA in Target Cells hardly affects EcoR Function Transferred by Gesicles.

(C) Transduction assay with GFP Ecotropic lentivectors in human cells treated with mCAT Gesicles. Cells treated by mCAT vesicles and bearing si-mCAT remain highly permissive to EcoLV transduction (87% of the control). This indicates that the EcoR function is mainly provided by the mCAT protein contained in microvesicles and not by contaminant mRNA nor plasmidic DNA.

Figure 8:
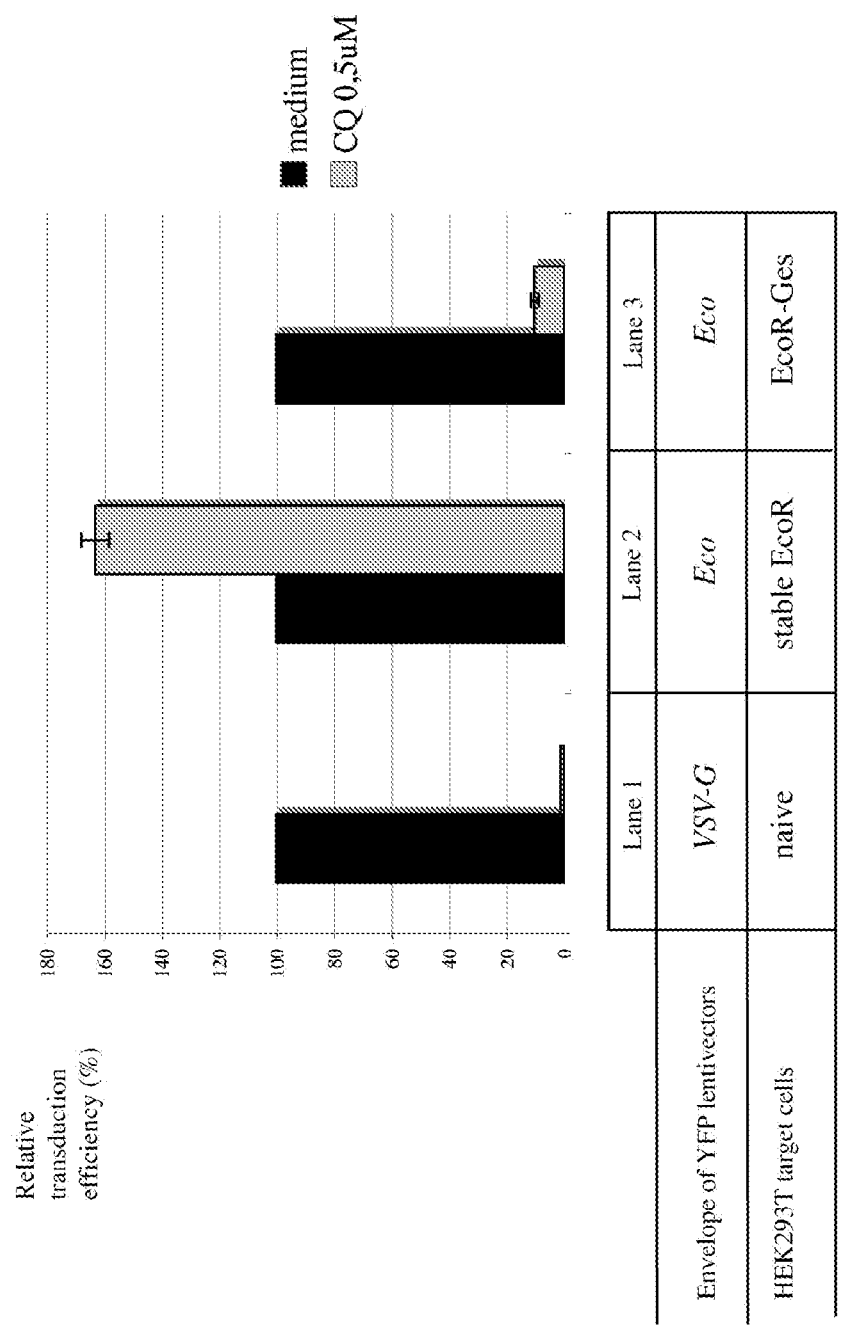

FIG. 8: Effect of Chloroquine on Ecotropic Lentiviral Transduction in Cells Modified by EcoR-Gesicles.

YFP-encoding lentiviral vectors pseudotyped with the Ecotropic envelope (Eco) were used to transducer HEK293T cells in which the mCAT-1 protein was delivered by EcoR Gesicles (EcoR-Ges) in the presence or absence of chloroquine (CQ), a drug raising the endosomal pH (lane 3). As a control, Ecotropic pseudotypes were used to transducer 293T cells in which the EcoR is stably expressed (stable EcoR, lane 2). To check the effect of CQ on endosomal acidification, VSV-G lentivectors were used to transduce target cells treated or not with the drug, illustrating the high pH-dependence of VSV-G pseudotypes (lane 1) while the ecotropic pseudotype remains efficient upon drug treatment. Results are given as the relative YFP transduction efficiency in the different cell types as measured by FACS 72 hours post-transduction.

Figure 9:
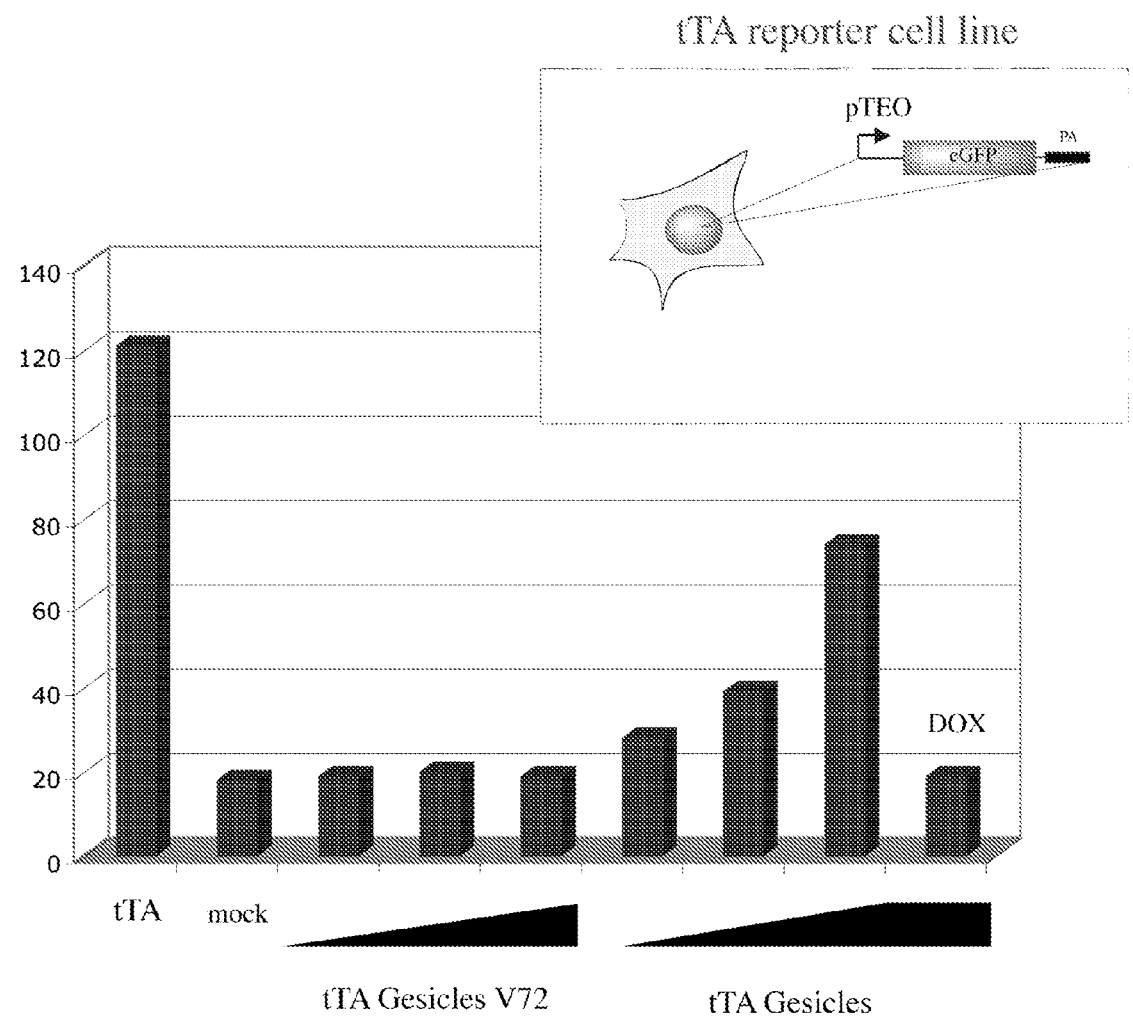

FIG. 9: Delivery of tTa by Gesicles

To detect the transcriptional function of the TET transactivating protein (tTAoff) we created a reporter cell line stably expressing eGFP under the control of the TET operator. Transfection of tTA activated the expression of eGFP in the reporter cell line (tTA lane) as compared to mock transfected cells. Gesicles produced in cells overexpressing tTA and VSV-G (wt) or its fusion incompetent mutant V72 were concentrated and laid on the reporter cell line at different doses. Increasing the dose of tTA Gesicles harbouring the wt VSV-G resulted in enhanced GFP expression. This signal could be abrogated by introduction of Doxycycline in the medium. Results are given as MFI analyzed by FACS 24 hours post-Gesicles.

Figure 10:
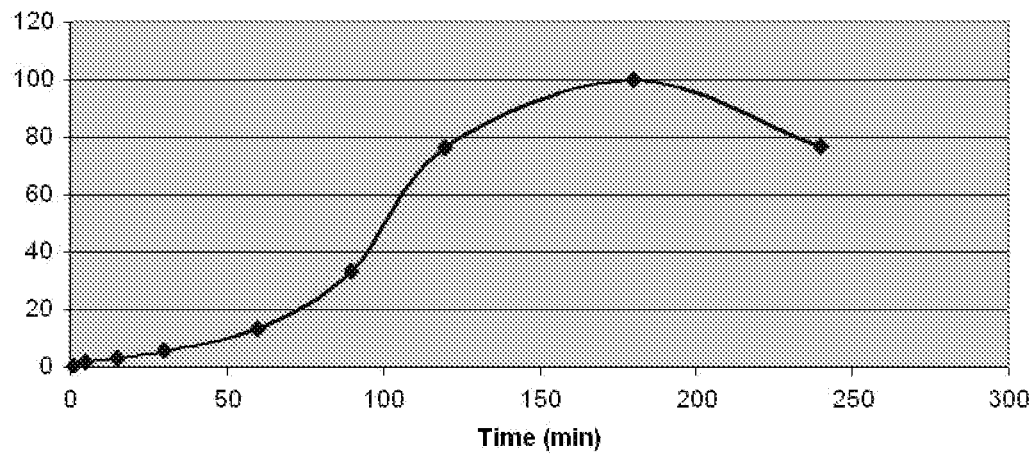

FIG. 10: Gesicle-Mediated tTA Transfer Efficiency as a Function of Time

The HEK reporter cell line Teo-GFP was plated in 12-well plates (1×10e5 cells per well) and treated with tTA Gesicles (50 μg of total protein). Exposure time ranged from 5 minutes to 4 hours. After exposure, the vesicle-containing medium was discarded and the cells washed with PBS and maintained in culture for a GFP analysis 24 hours later. tTA transfer efficiency raises gradually with time exposure up to 3 hours which is the optimal exposure time.

Figure 11:
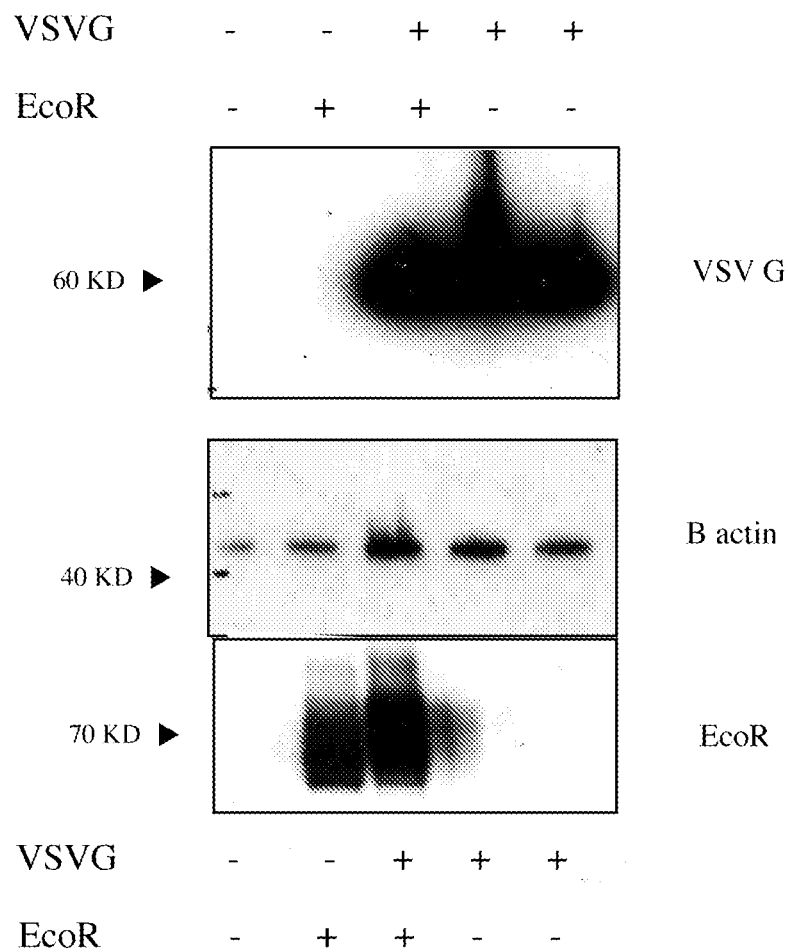

FIG. 11: VSV-G Protein Potentiates Vesicle Release and Protein of Interest Release from 293T Cells Membrane Protein Release:

WB analysis of mCAT-1, a multispanning membrane protein incorporated in vesicles produced with or without VSV-G Immunolabelling of mCAT-1 in the vesicle pellet shows that mCAT-1 release is dramatically increased when VSV-G is introduced in the producer cells.

Cytoplasmic Protein Release:

A similar biochemical analysis was performed on different batches of vesicle preparations, investigating the release of the cytoplasmic protein actin. We note that VSV-G sensibly potentiates actin release as compared to mock vesicles.

Figure 12:
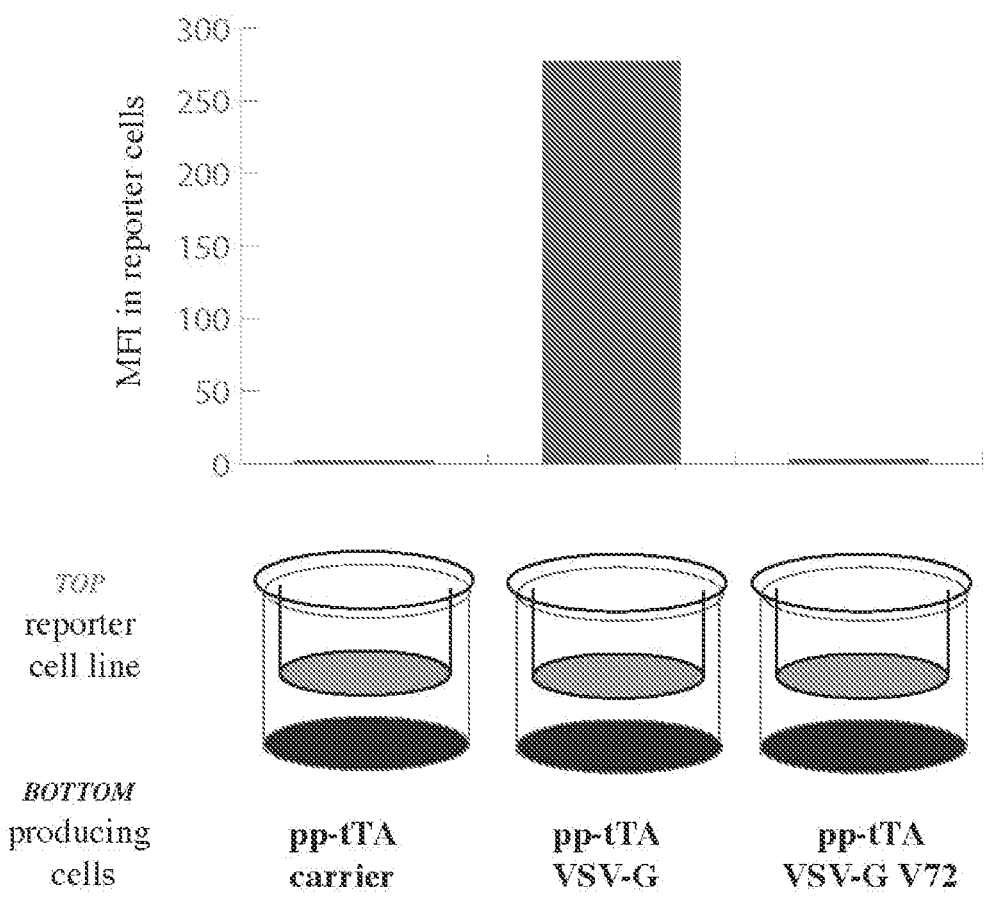

FIG. 12: Gesicle-Mediated Protein Transfer in a co-culture Experiment through 3 μm-pore Sized Inserts We cultivated in the same medium HEK cells transfected with various combinations of plasmids with the reporter Teo-GFP reporter cell line. Cells were separated by a 3 μm-pore sized filter as depicted, the producer cells in the bottom of a 6-well dish and the reporter cell line in the top insert. Producer cells were co-transfected with a tTA expression plasmid in addition with a carrier DNA, the VSV-G coding plasmid or a fusion defective VSV-G. After 48 hours of co-culture, inserts were removed and the reporter cell line trypsinized and analyzed by FACS to evaluate tTA delivery. Results are given as the MFI in the Teo-GFP cell line.

Figure 13:
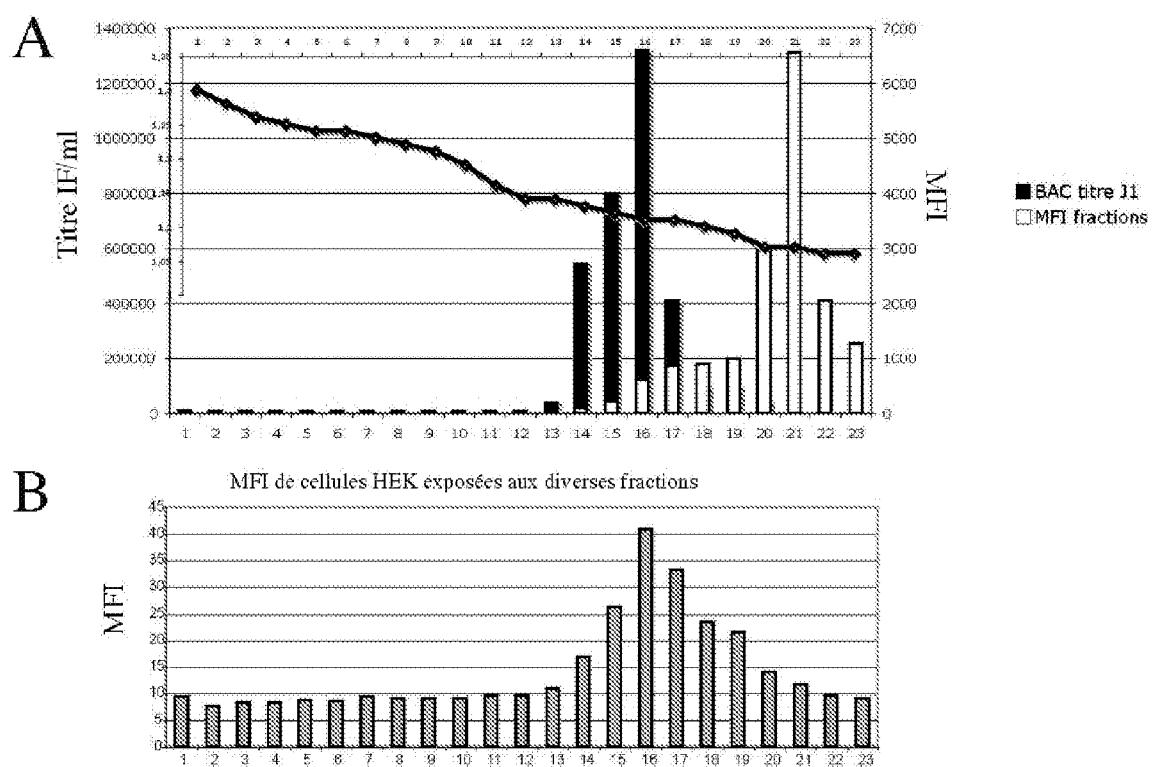

FIG. 13: Characterization of Insect Cell-Derived Microvesicles

GFP microvesicles were produced by infecting Sf9 cells for 72 hours with recombinant baculovirus. After concentration, they were laid on a iodixanol gradient and centrifuged for 10 h at 215000 g to allow sedimentation of vesicles according to their density. Fractions were collected from the bottom of the tube and their density was measured by weighing.

The density gradient can be appreciated on graph A, ranging from d=1.3 to d=1.05. All fractions were analyzed by a fluorometer to detect GFP (Exc 485 Em 515), essentially detected in fraction 21 (A, white bars). Dilutions of fractions were also used to infect sf9 cells to identify where the baculovirus sedimented. Three days after infection, sf9 cells were analyzed by FACS and Baculovirus titrated. Results given in A (black bars) indicated that the virus sedimented.

(B) The GFP transfer capacity of each fraction was analyzed. It was contained in fractions 14 to 19, overlapping partially the virus-containing fractions.

Figure 14:
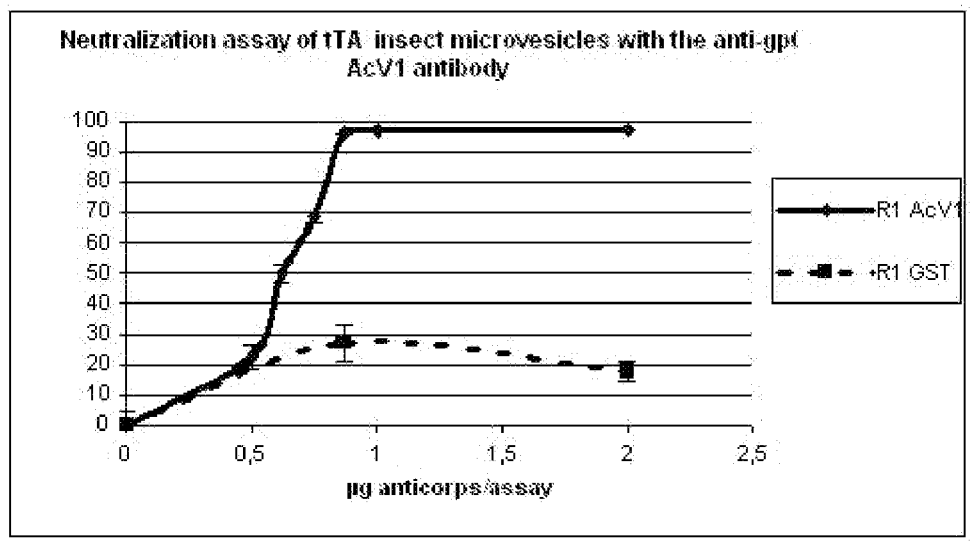

FIG. 14: Neutralization Assay (NA) of tTa Insect Microvesicles tTA microvesicles were produced in High5 cells infected with a tTA-baculovirus. Vesicles were concentrated and resuspended in PBS and diluted 10 times for the assay performed in 100 μl of PBS. 0.5 eq Phospholip tTA were incubated 2 h at 37° C. with serial dilutions of anti gp64 antibody (clone AcV1) or control antibody (GST). Vesicles were next laid on a HEK tTA reporter cell (expressing GFP once tTA is introduced in the cell). 24 hours later, vesicle-exposed cells were FACS-analysed and GFP expression was quantified. Results are given as the global population MFI.

Figure 15:
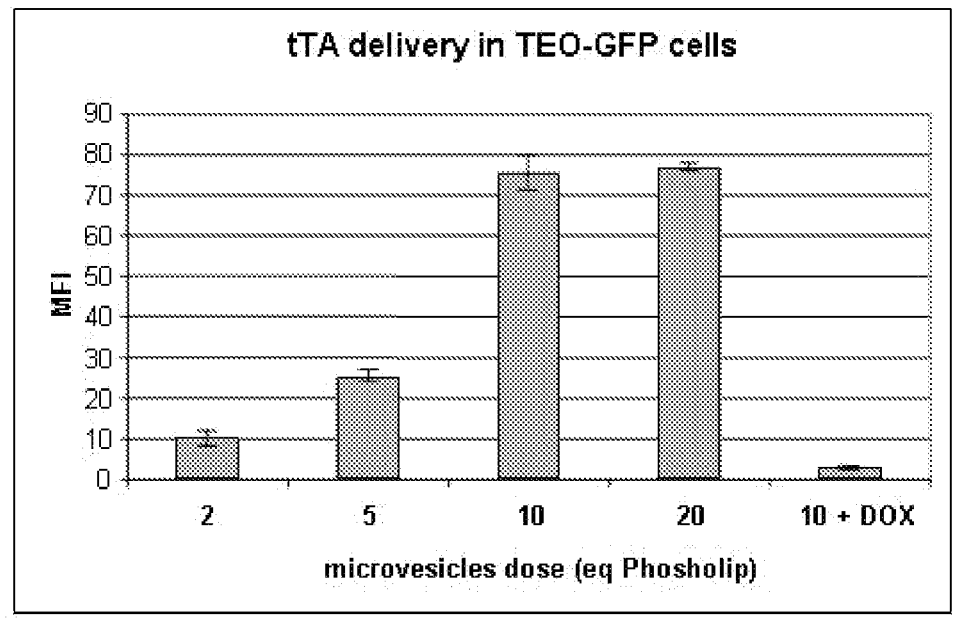

FIG. 15: Dose-Response using tTA Microvesicles tTA insect vesicles were concentrated and purified as described prior and stored at −80°. Increasing doses of vesicles were used to deliver tTA in a HEK tTA reporter cell line, resulting in an increased GFP signal detected in target cells 24 hours post-vesicles. Doxycycline-treated cells showed background fluorescence, reflecting the expected inducibility of the TET system.

Figure 16:
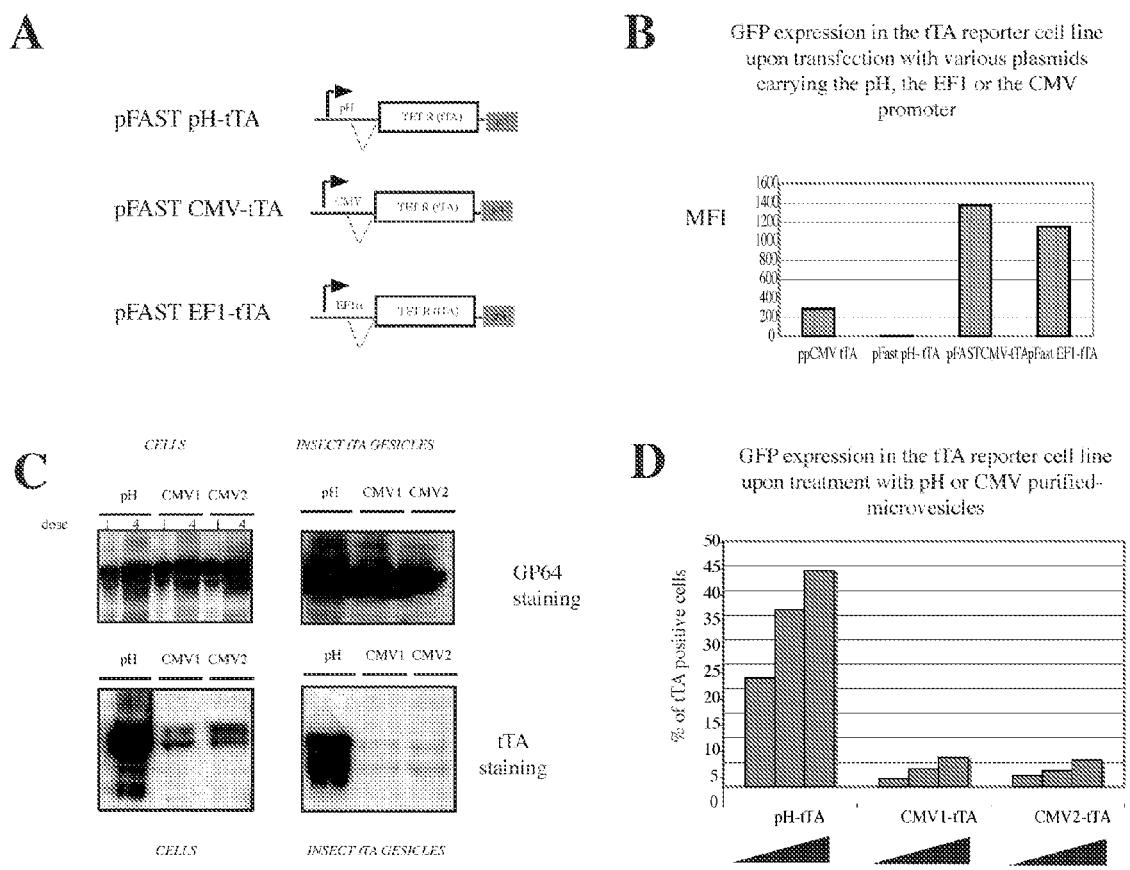

FIG. 16: Transfer of tTA in Human Cells is Achieved by Insect Cell-Derived Microvesicles and not by Coding Baculoviruses
 (A) Baculovirus constructs
 (B) GFP expression of promoter-driven tTA in tTA reporter cell line
 (C) release of GP64 and tTA into Gesicles
 (D) GFP expression in the tTA reporter cell line upon treatment with pH or CMV purified microvesicles.

EXAMPLES

Example 1

Abstract

The present example describes the engineering of exosome-like vesicles coated with the G glycoprotein of the Vesicular Stomatitis Virus (VSV-G) and used to deliver exogenous proteins in human target cells. These particles sediment at a density of 1.1 g/ml and can efficiently package cytoplasmic and membrane proteins as well as transcription factors. Model molecules including the membrane mCAT-1 protein and the tet transactivator were efficiently delivered in human target cells upon microvesicles treatment. Vesicle-mediated pseudotransduction led to transient protein expression and was not due to transfer of mRNA or DNA. We showed that chloroquine, a drug raising endosomal pH, invalidated protein transfer indicating that VSV-G induced fusion was involved in the delivery mechanism.

The VSV-G Fusogenic Envelope is a Key Determinant of Pseudotransduction

We tested whether expression of VSV-G could lead to the production of particles able to pseudotransduce. HEK-293T cells stably expressing YFP (293T-Y) were transfected by pVSV-G, a eukaryotic expression vector. Supernatants were collected two days later, filtered and concentrated by ultracentrifugation. As a control, the same process was applied to supernatants of mock transfected 293T-Y cells. The two concentrated preparations were added on naive 293T cells, which were washed after one hour of exposure. 24 hours later, cells were trypsinized and analysed by FACS to measure the fluorescence in the two populations. We were able to observe pseudotransduction of YFP in cells exposed to the VSV-G preparation and not in cells exposed to the control preparation (FIG. 1-B). Biochemical analysis of the two samples revealed that high amounts of YFP sedimented in the VSV-G preparation (FIG. 1-A lane 1) while YFP was almost undetectable in the mock transfected preparation (lane 5). These data indicate that VSV-G is responsible for the intense release of sedimentable particles containing components of the producer cell cytoplasm. Moreover, these particles appeared to be capable of delivering this material in target cells. As cells were washed upon treatment with particles and grown during 24 hours before trypsination and analysis, we assumed that the YFP signal is intracellular and not due to fluorescent adsorbed particles at the surface of the cells. These VSV-G microvesicles will be termed as Gesicles throughout example 1.

Additional Observations:

A VSVG single amino acid mutant unable to trigger fusion (VSVG V72) 14 was tested in this system and was not incorporated in the sedimented pellet (FIG. 1 lane 2). Another western blot experiment indicated that this mutant was expressed in producer cell but not detectable in the supernatant, as opposed to the wt-VSV-G detectable in both cells and supernatant (FIG. 1C). This demonstrates that production of VSV-G microvesicles requires a fusion competent form of VSV-G in the producer cell.

Pseudotransduction of the CD81 Tetraspanin Protein

The cell-to-cell transfer of a cytoplasmic protein such as YFP by a concentrated preparation supports the idea that 293T-Y cells have produced YFP-carrying vesicles surrounded by a lipid layer and possibly coated with others proteins of 293T cells like membrane proteins. To test this hypothesis we prepared a new batch of Gesicles by transfecting 293T cells with VSV-G and use this concentrated preparation to investigate the transfer of the CD81 protein, a tetraspanin protein characteristic of exosomes and abundantly expressed on 293T cells (FIG. 2 A). The resulting material was applied on HepG2 cells, a human liver cell line lacking CD81. We showed that HepG2 cells exposed to Gesicles for one hour stained positive upon a CD81 immuno-labelling, indicating that the protein was transferred from the producer to the target cell (FIG. 2. B).

The introduction of exogenous CD81 in HepG2 is known to allow transduction of this cell line by retroviral vectors pseudotyped with the HCV envelope (HCVpp) (Zhang. et al. *Journal of virology* 78, 1448-1455 (2004)). Indeed CD81 is described as one of the HCV receptors recognized by the E2 glycoprotein. Thus to further validate the CD81 transfer, we exposed HepG2 cells to various doses of Gesicles and checked their permissiveness to HCVpp-mediated transduction as compared with naive HepG2 cells. We showed that HepG2 permissiveness to HCVpp transduction increases with the amount of Gesicles introduced in cells (FIG. 2.C), increasing HCVpp titer up to 5 fold in this experiment. This shows that the transferred CD81 protein retains its HCV binding capacity even after transport and transfer via Gesicles.

Characterization of the YFP and CD81-Carrying Gesicles

To better characterize the material responsible for protein transfer, Gesicles were produced upon transfection of VSV-G in human cells cultivated with octadecyl rhodamine B chloride (R18), a lipophilic fluorophore labelling the membranes. After a first concentration step, R18-Gesicles were laid on a continuous iodixanol gradient and centrifuged 3 hours to allow separation of fractions according to their density. All collected fractions from 1 to 20 were analysed for their capacity to emit fluorescence at 590 nm after excitation at 560 nm, the emission and excitation values for R18. As shown in FIG. 3A, R18-fluorescence is detected in fractions 13 to 20 with a peak in fraction 17 which corresponds to a density of 1.11 g/ml.

In another experiment, Gesicles produced in 293T-Y were similarly processed and laid on a gradient prior analysis of YFP-associated fluorescence in the different collected fractions. FIG. 3B indicates that YFP was principally detected in fractions 17 and 18 corresponding to densities of 1.10-1.11. We next examined which fraction was able to deliver YFP by pseudotransduction. 1/10 of each sample was applied on 293T cells and fluorescence transfers were FACS-analysed 24 hours later. As shown in FIG. 3, the pseudotransduction determinant was essentially sedimented in fraction 17 (d=1.11). In another experiment, Gesicles were separated and analysed by Western blot. Analysis of density-fractions revealed that VSV-G and CD81 were clearly enriched in fractions 17 and 18 which correspond to densities of 1.10 and 1.11 g/ml (FIG. 2 D). As the CD81 molecule is described as a marker for exosomes (Lamparski et al. *Journal of immunological methods* 270, 211-226 (2002)) we can conclude that VSV-G-carrying Gesicles are a particular type of exosome-like vesicles.

Combined, our findings indicate that upon VSV-G transfection, HEK 293T cells produced membrane-surrounded Gesicles sedimentable at a density of 1.10-1.11 g/ml and that these exosome-like microvesicles contain proteins such as CD81 from the producer cells that are deliverable in target cells.

Gesicles-Mediated Transfer of mCAT-1 in Human Cells.

In the same manner as YFP or highly-expressed CD81 are packaged in Gesicles produced by 293T-Y/293T cells, we tested whether any protein overexpressed in the producer cell could be passively incorporated in nascent Gesicles and whether low amounts of this packaged material could be delivered in human target cells. This notion was tested using the mCAT-1 protein as a model, the murine cationic amino acid transporter also known as the receptor for the murine leukemia virus (MLV) Ecotropic envelope EcoRI. A plasmid encoding a flagged version of m CAT-1 was constructed (SwFlag EcoR depicted at FIG. 4) and cotransfected with VSV-G in 293T-Y cells to produce EcoR-bearing concentrated Gesicles subsequently introduced on human cells. After one hour, exposed cells were washed and stained positive for EcoR expression as revealed by a FACS analysis using an anti Flag-FITC antibody (not shown). To further validate the mCAT-1 transfer, we developed a transduction assay based on YFP-encoding lentivectors pseudotyped with the MLV-Ecotropic envelope. Due to the particular tropism of this glycoprotein, these lentivectors can transduce exclusively murine/rat cells or human cells in which mCAT-1 is expressed upon transfection. If EcoR-Gesicles efficiently deliver EcoR in human cells, these should become permissive to an Ecotropic YFP lentitransduction.

Results shown FIG. 4 give the titers of an Ecotropic lentivector preparation upon titration on human cells treated or not with EcoR Gesicles. While naive cells are restrictive to transduction with an Ecotropic lentivector (lane 3), cells treated with 2 µg (lane 1) or 4 µg (lane 2) of concentrated Gesicles become highly permissive to Ecotropic transduction. To avoid incorporation of Gesicles-G protein on Ecotropic lentivectors in the transduction medium, Gesicle-treated cells were washed twice prior transduction.

EcoR-Gesicles preparation was laid on a density gradient as previously described to identify the fraction responsible for the transfer of mCAT-1. Collected fractions were analysed by western blot and for their capacity to mediate EcoR transfer (FIG. 5). In this experiment, we show that fraction 17 corresponding to a density of 1.10 is highly enriched in VSV-G and mCAT-1 and is the main fraction responsible for EcoR transfer as revealed by a transduction assay. These data indicate that EcoR-Gesicles sedimenting at a density of 1.10 transferred the mCAT-1 protein in the membrane of target cells where it retains its binding property for the ecotropic envelope.

Moreover we show here that Gesicle content, and particularly the nature of proteins borne by the membrane of Gesicles can be easily controlled by transfection of producer cells.

Mechanistic of EcoR-Delivery by Gesicles
Lifetime of Transferred mCAT-1

We next examine the lifetime of the transferred mCAT-1 in human cells by varying the delay between the Gesicles exposure and the transduction assay. Results shown in FIG. 6 indicate that Eco receptor function disappeared from the 293T-cell surface around 50 hours after its Gesicle-mediated transfer. This experiment was reproduced on different human cell types including Hela, HUH.7 (not shown) without modification of the half-life of transferred mCAT-1 close to 24 hours. This transience comforts the notion that Gesicles deliver proteins and not plasmidic DNA that could contaminate the Gesicles preparation. Indeed encoding of mCAT-1 by plasmidic DNA would necessitate a transcription and a translation step in the target cells, leading to an expression peak 48 h after introduction as it is commonly observed for transfection experiments.

The EcoR Function is Provided by Ready-Made Proteins Incorporated in Gesicles.

To investigate the nature of the material transferred with the mCAT-1 vesicles, we treated human target cells with a siRNA directed against the mCAT-1 mRNA. Should the vesicles deliver mRNA or DNA encoding it, it would be rapidly degraded in si-mCAT treated cells.

As revealed by a mCAT-1 immunostaining (FIG. 7A), the mCAT-1 siRNA suppressed mCAT expression upon a cotransfection experiment in HEK cells. Moreover, introduction of this specific siRNA in cells transfected with a mCAT-1 plasmid strongly decreased the capacity of cells to be transduced with ecotropic lentivectors (FIG. 7B). While VSV-G pseudotyped lentivectors (gLV) transduced efficiently both si-CTL and si-mCAT cells, the transduction efficiency achieved with ecotropic lentivectors (EcoLV) was inhibited in si-mCAT cells (70% of inhibition). These data indicate that the si-mCAT impacts specifically on the mCAT-1 receptor function when this is coded by a plasmid.

We next examined whether the mCAT-siRNA affected the receptor function delivered by mCAT-1 microvesicles. Cells were transfected with mCAT and control siRNAs and treated with mCAT-1 vesicles 48 hours later. A transduction assay was next performed with EcoLV to check the receptor function (FIG. 7C). Both si-CTL and si-mCAT cells were efficiently transduced with EcoLV, indicating that the si-mCAT largely failed in suppressing the receptor function delivered by vesicles. This indicates that microvesicles essentially delivered the receptor function by transferring ready-made proteins and not mRNA or contaminating plasmid DNA.

Gesicle-Mediated EcoR Delivery is pH-Dependent

Since the transferred EcoR protein is functional as a viral receptor, this implies its presence at the surface of the target cell. However, due to the nature of the VSV-G envelope, fusion between Gesicles and cell membrane is expected to take place in the internal acidic compartments, liberating the EcoR protein inside the cell and not at the surface where it is functional.

To gain insights in the mechanism of EcoR-transfer, we treated 239T target cells with chloroquine (CQ) before Gesicles treatment, a drug raising endosomal-pH and known to disrupt membrane fusion triggered by VSV-G. As shown in FIG. 8, VSV-G-pseudotyped lentivectors are unable to transduce CQ-treated cells (lane 1) while Ecotropic lentivectors remain efficient when used on drugged-293T expressing constitutively mCAT-1 (lane 2). These data illustrate the pH-dependence. Interestingly we show that CQ strongly inhibits EcoR-delivery by gesicles (lane 3). Since transduction with ecotropic reporter lentivectors is not decreased by CQ, this result reflects a CQ-mediated failure in the cell mechanism delivering EcoR at the surface.

Considering these data, we propose a model where Gesicles after being internalized in the target cell are transported in the endosomal compartments where fusion of membranes is required for EcoR release. The proteins, following the fate of many endogenous receptors, would be subsequently recycled toward the cell membrane.

Gesicle-Mediated Delivery of the TET Transactivator

Besides delivery of cytoplasmic and membrane proteins, we explored the capacity of Gesicles to package and deliver transcription factors, proteins classically expressed in the nucleus. For this purpose Gesicles were produced in 293T cells cotransfected with a plasmid encoding the TETofftransactivator (tTA), a synthetic transcription factor activating transcription of its cognate promoter the Tet operator (TEO) and that can be switched-off by introduction of tetracycline/doxycycline in the cell culture medium (Gossen et al., *Proceedings of the National Academy of Sciences of the United States of America* 89, 5547-5551 (1992)). Increasing doses of tTA loaded gesicles were next laid on reporter cells harbouring an expression cassette composed of the eGFP gene under the control of the Tet operator. Result shown in FIG. 9 indicate that fluorescence of the reporter cell line is activated by tTA Gesicles 24 hours after treatment. Fluorescence signal increases with gesicle-doses and reaches for the highest dose around 50% of the signal obtained in a reporter cells transfected with a tTA construct. We note that transcription activation in the treated cells remains sensible to Doxycycline treatment. This indicates that the tet transactivator protein has been successfully packaged in Gesicles and transferred in the reporter cell line.

Gesicle Mediated tTA Transfer Efficiency as a Function of Exposure Time

The HEK reporter cell line Teo-GFP was plated in 12 well plate ($10^5$ cells) and treated with tTA gesicles (50 µg of total protein per well). Exposure time ranged from 5 minutes to 4 hours. After exposure, vesicle-containing medium was discarded; cells were washed with PBS and maintained in culture for a GFP analysis 24 hours later. tTA transfer efficiency raises gradually with time exposure up to 3 hours which is the optimal exposure time (see FIG. 10).

Gesicles Production and Dosage Methods

Human EcoR-Gesicles Production and Dosage

Human gesicles were produced by transfection of HEK 293T cells using the calcium phosphate method. Cells were seeded at $3 \times 10^6$ cells in 10 cm dishes and cotransfected with 15 µg of a VSV-G encoding plasmid and 15 µg of the mCAT-1 encoding plasmid per dish. Transfection medium was replaced 24 h later by fresh media containing ATP (100 µM) and vesicles-containing supernatant were collected 48 hours and 72 hours after transfection, pooled, filtered through a 0.45 um filter, and ultracentrifuged 1H30 in a SW41 rotor at 25000 rpm (110000 g). Alternatively concentration can be performed at 4500 g for 10 hours. Pelleted material was finally resuspended in cold PBS resulting in a 200-fold concentration. Large preparations were performed using six 10-cm dishes and generated around 400 ul of 200X vesicles.

YFP/CD81 carrying vesicles were produced by transfecting 15 µg of VSV-G plasmid in HEK-293T cells previously transduced by a YFP-expressing lentivector.

To quantify the amount of proteins in sedimented microvesicles, we developed an ELISAssay detecting the flagged mCAT-1 protein. Briefly, serial dilutions of vesicles were lysed in PBS/Triton X100 2% and coated overnight in a 96-well plate (NUNC.Maxisorp) in a carbonate coating buffer (pH 9.6). Serial dilutions of the flag-peptide (Sigma) were coated in parallel in a Triton-free buffer. Proteins and peptide were revealed upon 1 h-incubation of the washed plate with an anti-Flag-HRP antibody diluted at 1/1000 (M2 Sigma) and a final revelation with the TMB substrate. These assays allowed us to dose the amount of flagged-protein in the vesicle-preparation.

Alternatively, we engineered a VSV-G Elisa assay by coating serial dilutions of the VSV-G peptide recognized by the anti-VSVG antibody coupled with HRP (P5D4. Sigma). Thus all VSV-G vesicles can be expressed as an equivalent mass of VSV-G peptide per microliter of the vesicle preparation.

Discussion

We developed here an original and simple way to transfer cytoplasmic and membrane proteins in human cells by the use of engineered exosome-like vesicles. This Gesicle-mediated protein delivery technology was further used to introduce a functional transcription factor in human cells. Production of these microvesicles was achieved by overexpression of the protein of interest in 293T producer cells cotransfected with VSV-G. VSV-G appears to boost vesicles production from 293T cells as revealed by the analysis of supernatants enriched in membrane proteins as well as membrane lipids and actin (FIG. 11). Furthermore, by coating the membranes of microvesicles, the fusogenic G protein enhances their ability to contact target cells and allows very efficient fusion between particles and cell membranes, a prerequisite for the release of the microvesicle content in the target cells.

Example 2

Vesicle-mediated protein transfer in a coculture experiment through 3-µm pore sized inserts.

We cultivated in the same media HEK cells transfected by various combinations of plasmids, together with the Teo-GFP reporter cell line. Cells were separated by a 3-µm pore sized filter as depicted, the producing cells in the bottom of a 6-well dish and the reporter cell line in the top insert. Producing cells were cotransfected with a tTA expression plasmid in addition with a carrier DNA, the VSV-G coding plasmid or a fusion defective VSV-G. After 48 hours of coculture, inserts were removed and the reporter cell line trypsinized and analysed by FACS to evaluate tTA delivery. Results are given as the MFI in the Teo-GFP cell line (FIG. 12).

This technique enables the delivery of protein into target cells, without the need of a concentration step. Concentrated vesicles can be toxic depending on the target cell type. Target cells can be cultivated in the top or the bottom chamber and infused several days with vesicles producing-cells for a constant protein delivery. Successive infusions can even be performed if several factors have to be introduced sequentially by easy transfer of the insert in another vesicle-containing bath.

Example 3

Insect Cells Microvesicle Production and Dosage

Baculovirus production was performed using the Bac-to-Bac Baculovirus expression system (Invitrogen) according to the manufacturer's instructions. Briefly, cDNAs of interest were cloned in the pFAST-1 shuttle prior to recombination in DH10-BAC bacteria. Baculovirus DNAs were next used to transfect SF-9 cells to generate the first baculo stock collected 72 hours later (passage 1). This polyclonal stock was further amplyfied to reach a titer of $1 \times 10^7$ pfu/ml (passage 2) that was stored at 4° C. and used for vesicles production.

Insect cells microvesicles were produced upon baculovirus infection (MOI 0.5-1) of $200 \times 10^6$ HIGH5 cells cultivated in suspension at 30° C. under agitation in 100 ml of Express-five SFM media supplemented with Glutamine (20 mM) and Penicillin-Streptomycin (25 U of penicillin, 25 µg of Streptomycin/nil). 48 hours after inoculation, medium was harvested clarified and filtered twice through a 0.45 µm pore-sized filter prior to ultracentrifugation in a SW-32 rotor at 24000 rpm (100.000 g). Sedimented material was next resuspended in cold PBS (100× concentration) and stored at −80° C.

For a better purification, this cloudy preparation was laid on a discontinuous iodixanol gradient to allow separation of discrete density fractions. Biological analysis of fractions revealed that active vesicles able to transfer harboured proteins sedimented at a density between 1.09-1.11. Highly purified vesicles were prepared upon pooling these fractions and after a last concentration step of the pool supplemented with cold PBS (1 h at 30000 rpm in SW41).

Insect cell-derived vesicles were quantified with the phospholipid-enzymatic PAP50 detection kit (Biomérieux) and with the VSV-G ELISA described above.

Characterization of Insect Cell Derived Microvesicles

GFP microvesicles were produced as described upon infection of sf9 cells for 72 h with a recombinant baculovirus. After concentration, vesicles were laid on an iodixanol gradient and centrifuged at 215000 g for 10 h to allow sedimentation of vesicles according to their density. Fractions were next collected from the bottom of the tube and their density was measured by weighing. The density gradient can be appreciated on the graph of the FIG. 13 A, ranging from d=1.3 to 1.05. All fractions were analysed by a fluorometer to detect GFP (Exc 485 Em 515) essentially detected in fraction 21 (FIG. 13 A white bars). Dilutions of fractions were also used to infect sf9 cells to identify where the GFP Baculovirus sedimented. Three days after infection, sf9 were analysed by FACS and the Baculovirus titer was calculated. Results given in A (black bars) indicated that the virus sedimented between fraction 13 and fraction 20 with a peak for fraction 16. We also used the fractions to deliver GFP in human cells and analysed fluorescence transfer 24 h latter (FIG. 13 B). Interestingly, we found that the GFP transfer capacity was contained in fractions 14 to 19, overlapping in part the virus containing fractions.

Neutralization Assay (NA) of tTA Insect Microvesicles.

tTA microvesicles were produced in High5 cells infected with a tTA-baculovirus. Vesicles were concentrated and resuspended in PBS and diluted 10 times for the assay performed in 100 μl of PBS. 0.5 eq Phospholip tTA were incubated 2 hours at 37° C. with serial dilutions of anti gp64 antibody (clone AcV1) or control antibody. Vesicles were next laid on a HEK tTA reporter cell (expressing GFP once tTA is introduced in the cell). 24 hours later, vesicle-exposed cells were FACS-analysed and GFP expression was quantified. Results (see FIG. 14) are given as the global population MFI.

Dose Response using tTA Insect Microvesicles.

tTA insect microvesicles were concentrated and purified as described previously and stored at −80° C. Increasing doses of vesicles were used to deliver tTA in a HEK tTA reporter cell line, resulting in an increasing GFP signal detected in target cells 24 hours post-vesicles. Doxycycline-treated cells showed background fluorescence, reflecting the expected inducibility of the TET system (see FIG. 15).

Discussion

We have shown that production of human cell derived vesicles was achieved upon cotransfection of producer cells with the VSV-G coding plasmid and another plasmid encoding the protein of interest (YFP, mCAT-1, tTA . . . ). To increase the performance of the production system, we constructed recombinant baculoviruses encoding VSV-G and tTA and infected insect cells highly permissive to baculovirus infection. Moreover High5 cells and SF9 cells can be cultivated easily in suspension up to $2\times10^6$/ml without serum or even in synthetic media devoid of animal product. Notably, baculoviruses do not replicate in human cells and the polyhedrin promoter driving expression of the transgene is insect cell specific and not active in human cells.

We found that upon coinfection with tTA and VSVG, insect cells produced microvesicles able to transfer tTA in human cells. We also found that VSV-G was useful but dispensable in this process, suggesting that another fusion protein could replace it. This role could be assumed by gp64, the envelope glycoprotein of Baculovirus that is expressed in all infected cells. By performing a neutralization assay, we have shown that protein delivery mediated by insect microvesicles could be neutralized by a gp64 antibody.

To further characterize insect cell vesicles, we laid GFP insect-vesicles on an iodixanol gradient to measure their density. This process allows separation of different materials present in a mixture according to their respective density. This experiment indicated that the vesicle-containing fraction was overlapping with the baculovirus-containing fractions. It is commonly admitted that baculovirus cannot replicate in human cells, however we can imagine that a slight expression of tTA coding baculoviruses could produce enough tTA to activate the GFP expression in the reporter target cells. To check this, we replaced the insect specific polyhedrin promoter (pH) by the CMV or the EFIa promoter in the shuttle plasmid (pFAST) used to construct the Bac recombinant (constructs depicted in FIG. 16 A). As opposed to pH, those promoters are highly active in human cells as revealed by a transfection experiment in the HEK-Teo GFP reporter cell line (FIG. 16 B). We next chose the CMV promoter to generate two recombinant baculoviruses (CMV1 and CMV2) subsequently amplified and used to infect in sf9 cells. Both CMV recombinants infected sf9 cells as efficiently as the pH recombinant. This was revealed by a western blot analysis performed on producer cells lysates (FIG. 16 C). The baculovirus protein gp64 was clearly detected in cell lysates regardless the nature of the promoter used. Upon microvesicles preparation, we performed the same staining on microvesicle lysates and verified that gp64 was highly detected in the three samples, showing that the CMV replacement did not significantly affect neither baculovirus infection in sf9 nor virus-release. As expected, we found that the pH recombinant expressed higher levels of tTA in sf9 cells as compared with the two CMV recombinants. This logically impacted the tTA amount detected in microvesicles, considerably higher in the pH lysates. Increasing doses of pH-tTA and CMV-tTA microvesicles were finally laid on the HEK-TeoGFP cell line. MFI reflecting the efficacy of tTA delivery was analysed by FACS 24 h later revealing that the vesicles produced with the pH recombinant were ten-fold more efficient than those produced with the CMV recombinants (FIG. 16 D). This shows that an efficient tTA transfer correlates with high levels of protein expression in the producer cells. This supports the hypothesis that the protein itself is transmitted by baculovirus associated microvesicles. Moreover, increasing the transcription performance of the tTA baculovirus in the human cell by promoter swapping does not increase tTA availability in the target, showing that Baculovirus-driven transcription is not responsible (or poorly involved) of the delivered tTA function. Altogether these data show that transfer of tTA in human cells is achieved by insect-cell derived gp64 microvesicles and not by coding baculoviruses.

REFERENCES

Throughout this application, various references describe the state of the art to which this invention pertains. The disclosures of these references are hereby incorporated by reference into the present disclosure.

The invention claimed is:

1. An in vitro method of delivering a protein of interest into a target cell comprising culturing a target cell with an isolated eukaryotic cell overexpressing a viral membrane fusion protein and a protein of interest, wherein said eukaryotic cell secretes microvesicles comprising said viral membrane fusion protein and a protein of interest, wherein said eukaryotic cell does not express any viral structural proteins and said protein of interest is not covalently bonded to said viral membrane fusion protein, and wherein said microvesicles secreted by said eukaryotic cell contact said target cell and deliver said protein of interest into said target cell.

2. The method according to claim 1, wherein several proteins of interest are delivered into said target cell by culturing said target cell with several of said eukaryotic cell each overexpressing a different protein of interest.

3. The method according to claim 1, wherein said protein of interest is a membrane receptor.

4. The method according to claim 1, wherein said protein of interest is a transcription factor.

5. A method of rendering a target cell transiently permissive to an ecotropic viral particle comprising contacting a target cell with a microvesicle comprising a viral fusion protein and an ecotrophic viral receptor (EcoR), wherein said contacting delivers said EcoR into said target cell and renders said target cell transiently permissive to an ecotropic viral particle, wherein said microvesicle is produced by an isolated eukaryotic cell overexpressing a viral membrane fusion protein and said EcoR, wherein said eukaryotic cell secretes said microvesicles, and wherein said eukaryotic cell does not express any viral structural proteins and said EcoR is not covalently bonded to said viral membrane fusion protein.

* * * * *